(12) United States Patent
Warren

(10) Patent No.: US 8,471,051 B2
(45) Date of Patent: Jun. 25, 2013

(54) C-H BOND AMINATION AND OLEFIN AZIRIDINATION WITH β-DIKETIMINATO COPPER CATALYSTS

(75) Inventor: Timothy H. Warren, McLean, VA (US)

(73) Assignee: Georgetown University, Washington, DC (US)

(*) Notice: Subject to any disclaimer, the term of this patent is extended or adjusted under 35 U.S.C. 154(b) by 678 days.

(21) Appl. No.: 12/518,189

(22) PCT Filed: Dec. 5, 2007

(86) PCT No.: PCT/US2007/086506
§ 371 (c)(1),
(2), (4) Date: Nov. 10, 2009

(87) PCT Pub. No.: WO2008/073781
PCT Pub. Date: Jun. 19, 2008

(65) Prior Publication Data
US 2010/0056806 A1    Mar. 4, 2010

Related U.S. Application Data

(60) Provisional application No. 60/873,321, filed on Dec. 7, 2006.

(51) Int. Cl.
| | |
|---|---|
| *C07F 1/08* | (2006.01) |
| *C07F 15/06* | (2006.01) |
| *C07D 203/04* | (2006.01) |
| *C07C 209/00* | (2006.01) |
| *C07C 233/00* | (2006.01) |

(52) U.S. Cl.
USPC ........... 556/110; 556/138; 548/954; 564/123; 564/469

(58) Field of Classification Search
USPC ............ 556/110, 138; 564/123, 469; 548/954
See application file for complete search history.

(56) References Cited

FOREIGN PATENT DOCUMENTS
WO    WO 2005/007659 A2    1/2005

OTHER PUBLICATIONS

Badiei et al. "Electronic structure and electrophilic reactivity of discrete copper diphenylcarbenes" Journal of Organometallic Chemistry, 2005, vol. 690, pp. 5989-6000.*
Laitar et al. "Copper(I) Complexes of a Heavily Fluorinated β-Diketiminate Ligand: Synthesis, Electronic Properties, and Intramolecular Aerobic Hydroxylation" Inorganic Chemistry, 2003, vol. 42, pp. 7354-7356.*
Spencer et al. "Copper Chemistry of β-Diketiminate Ligands: Monomer/Dimer Equilibria and a New Class of Bis(μ-oxo)dicopper Compounds" Inorganic Chemistry, 2002, vol. 41, pp. 6307-6321.*
Ph.D. Dissertation, North Carolina State University, 2005, Synthesis and Reactivity of Ruthenium and Platinum Amido and Carbene Complexes: Application Toward Carbon-Nitrogen Bond Forming Reactions, (Zhang), p. 39.
International Search Report for PCT/US07/086506 mailed Aug. 1, 2008.

* cited by examiner

Primary Examiner — Joseph Kosack
(74) Attorney, Agent, or Firm — Foley Hoag LLP

(57) ABSTRACT

One aspect of the present invention relates to a method for the transition metal (e.g., Cu(I)) mediated amidation of C—H bonds using electron-rich aliphatic azides. In certain embodiments, the methods are useful for the C—H insertion of nitrenes generated and stabilized by a β-diketiminato metal catalyst. In certain embodiments, said nitrenes are generated from organoazides, or by oxidation of the corresponding amine. Another aspect of the present invention relates to olefin aziridination using said β-diketiminato metal catalysts. In addition, the methods of the present invention include stereoselective C—H bond aminations and olefin aziridinatons. In certain embodiments, the methods are conducted in an aerobic environment. In certain embodiments, the present invention relates to the use of $O_2$ as an oxidant, wherein water is the byproduct of oxidation; this fact avoids the generation of toxic byproducts and renders the methods atom economical.

26 Claims, 13 Drawing Sheets

Figure 10

| substrate | product | yield | time | 1 equiv. in benzene yield | 5 equiv. yield |
|---|---|---|---|---|---|
| toluene | PhCH₂-NHAd | 95%[a] | 5 hr | 31 % | 49 % |
| ethylbenzene | PhCH(CH₃)-NHAd | 94 %[b] | 5 hr | 82 % | 85 % |
| indane | 1-NHAd-indane | 93 %[b] | 1 hr | 80 % | |
| cumene | PhC(CH₃)₂-NHAd | 95 %[a] | 24 hr | 50 % | |
| cyclohexane | Cy-NHAd | 90%[b] | 48 h (1.5 hr)[c] | 32 % | 40 % |
| benzaldehyde | PhC(O)-NHAd | | 24 hr | | 90%[d] |

[a]Yields determined by ¹H NMR. [b]Isolated yields. [c]Reaction carried out by microwave assisted radiation T = 120 °C with 2.5 mol % of catalyst. [d] Estimated by GC/MS.

Figure 12
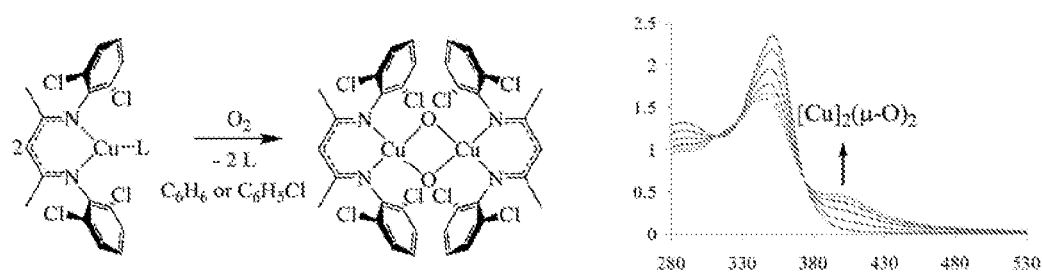
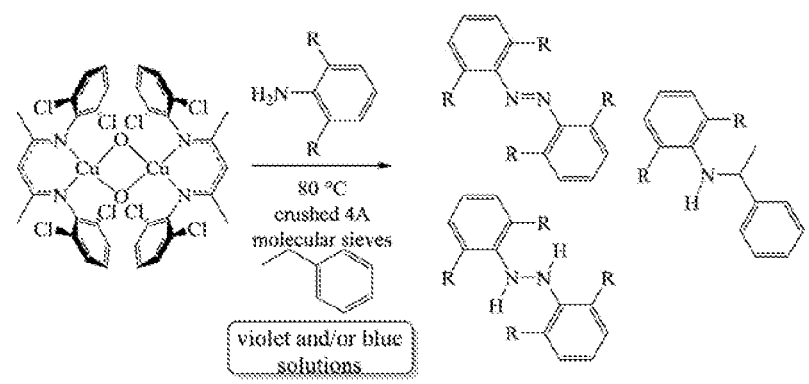

C-H BOND AMINATION AND OLEFIN AZIRIDINATION WITH β-DIKETIMINATO COPPER CATALYSTS

RELATED APPLICATIONS

This application is a 371 national stage application based on Patent Cooperation Treaty Application serial number PCT/US2007/086506, filed Dec. 5, 2007; which claims the benefit of priority to U.S. Provisional Patent Application Ser. No. 60/873,321 filed Dec. 7, 2006; the entireties of both of which are hereby incorporated by reference.

GOVERNMENT SUPPORT

The invention was made using support provided by the National Science Foundation (CHE-0135057); therefore, the government has certain rights in the invention.

BACKGROUND OF THE INVENTION

The insertion of a nitrene (NR) into a C—H bond is a transformation with great synthetic promise. The conversion of a C—H bond into an amine offers a way to introduce a N-atom into an organic molecule. Since most organic molecules contain C—H bonds, such a method would allow for the insertion of a NR group into many organic molecules. More traditional means of adding a N atom into an organic molecule generally require the presence of a functional group such as a C—X (X=halogen, pseudohalogen, or OR) or the presence of a double bond (C=O, or C=C-hydroamination). See Godula, K. and Sames, D. (2006) *Science*, 312:67-72; Cenini et al (2006) *Coord. Chem. Rev.*, 250:1234-1253; Halfen, J. A. (2005) *Curr. Org. Chem.*, 9:657-669; Davies, H. M. L. and Long, M. S. (2005) *Angew. Chem. Int. Ed.*, 44:3518-3520; Müller, P. and Fruit, C. (2003) *Chem. Rev.*, 103:2905-2919.

Transition metal-catalyzed C—H bond amination generally involves generation of a nitrene (NR) in the presence of a transition metal catalyst [M] which is thought to stabilize it against the generally non-selective reactivity of free nitrenes (Davies and Long, Ibid.) This transition metal-stabilized nitrene [M]=NR or [M]₂(μ-NR) then undergoes further reaction with an organic substrate more selectively than the free nitrene.

Two main modes of reactivity have been observed for transition metal catalyzed reactions of nitrenes. Addition to unsaturated organic molecules such as alkenes may be observed, giving rise to aziridines. This produces a valuable family of strained, three-membered rings containing one N atom, which appear in biologically active compounds and also serve as versatile synthetic intermediates to more complex structures owing to facile ring opening by a variety of nucleophiles. A competing mode of reactivity is insertion into C—H bonds. The factors that control this selectivity are not entirely clear, and some catalysts that serve as effective aziridination catalysts also perform catalytic C—H amination (Scheme 1).

Ru-porphyrin complexes such as that depicted in Formula I have been used to perform intermolecular catalytic amination of C—H bonds with sulfonylnitrene precursors such as PhI=NTs. Discrete [Ru]=NTs and [Ru](=NTs)₂ species have been isolated, and shown to react with olefins to give aziridines or C—H bonds to give amines, and it has been shown that the rate depends on the strength of the C—H bond being activated, with weaker C—H bonds undergoing faster amination. See Leung et al. (2005) *JACS*, 127:16629-16640; Au et al. (1999) *JACS*, 121:9120-9132.

Formula I.

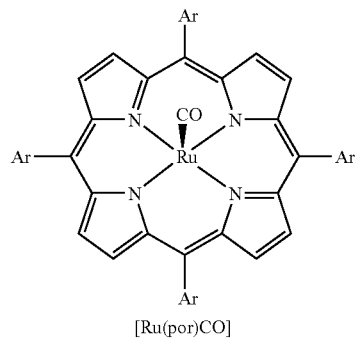

[Ru(por)CO]

Ar groups

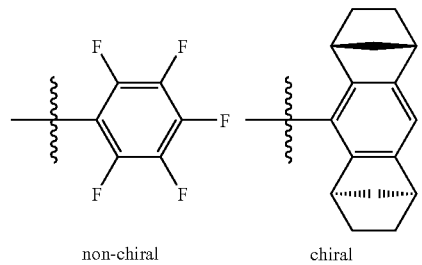

non-chiral     chiral

A copper-based system with brominated tris(pyrazolyl)borate ligands has also shown significant activity in intermolecular C—H amination reactions (Scheme 2). See Fructos et al. (2006) *JACS*, 128:11784-11791; Díaz-Requejo et al. (2003) *JACS*, 125:12078-12079. It is also a very good aziridination catalyst with many olefins to give N-tosylaziridines. See Díaz-Requejo et al. (1997) *Organometallics*, 16:4399-4402; Díaz-Requejo et al. (2001) *J. Organomet. Chem.*, 617-618:110-118; Mairena et al. (2004) *Organometallics*, 23:253-256. Since rates of C—H amination are controlled by the strength of the C—H bonds, benzylic and substituted benzylic C—H bonds serve as efficient reaction partners with PhI=NTs. What is significant is the reasonable yield with cyclohexane, a substrate containing only secondary C—H bonds. Amidation of aromatic C—H bonds is also possible. Reaction of PhI=NTs with benzene gives PhNHTs in 80% yield. Electron-poor phenanthroline ligands in conjunction with Cu(I) salts allows for the tosylamination of electron-rich Scheme 1.

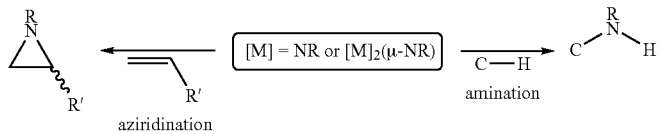

phenyl rings such as 1,3-(MeO)$_2$C$_6$H$_4$ in 63% yield. See Hamilton et al. (2004) *Chem. Commun.*, 1628-1629.

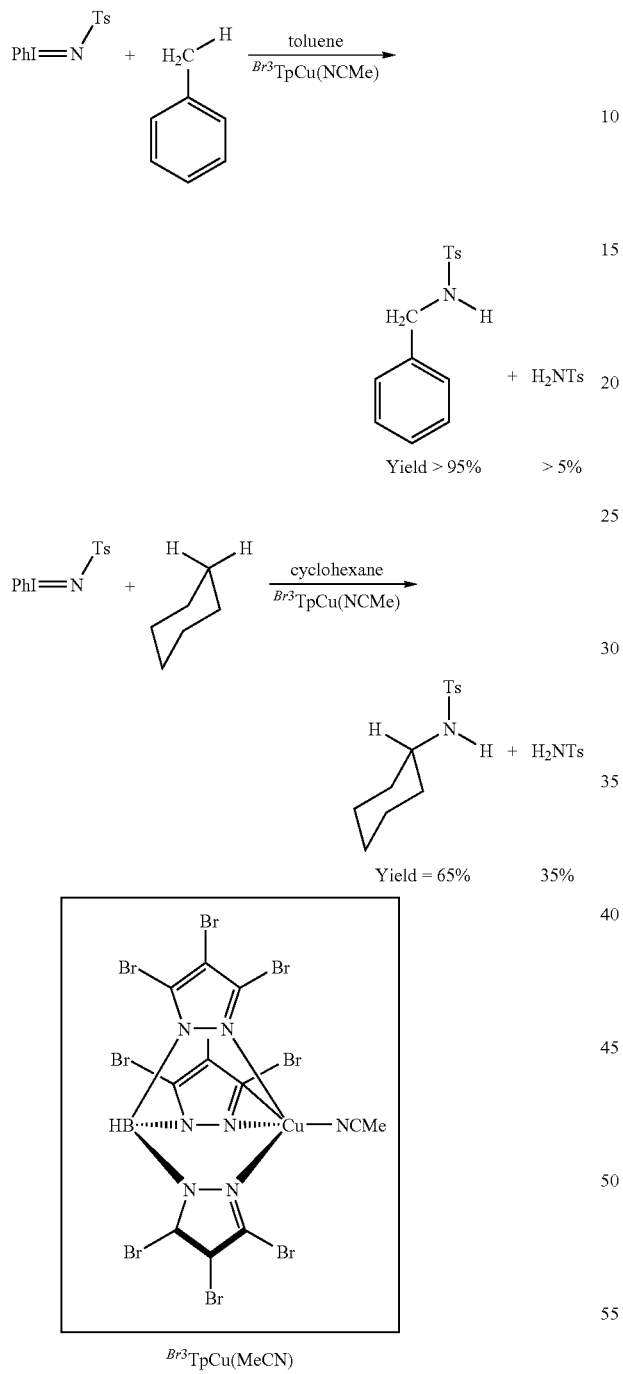

However, there are a number of limitations associated with these methodologies. For example, (1) they often require the use of tosyl imides, or electron-poor N-substituents; and (2) the PhI=NTs or NaNTsCl precursors must be isolated before use, the later of which is commercially available (See Fructos, supra).

More recent advances describe the in situ generation of an iminoiodane PhI=NR for use in transition metal catalyzed C—H nitrene insertion by reaction of a amine H$_2$NR bearing very electron withdrawing —SO$_2$R, C(O)OR, or C(O)CF$_3$ substituents R. See Davies (supra); Dodd, R. H., and Daubon, P. (2003) *Synlett.*, 11. This has been exploited for a powerful intramolecular variant of the C—H bond amination reaction leading to the formation of 5- and 6-membered N-containing heterocycles. One of the key features of this reaction is that C—H bond insertion proceeds with retention of configuration. See Davies (Ibid.); Liang et al. (2006) *Angew. Chem. Int. Ed.*, 45:4641-4644; Du Bois, J. and Hinman, A. (2003) *JACS*, 125:11510-11511; Espino, C. G. and Du Bois, J. (2001) *Angew. Chem. Int. Ed.*, 40:598-600. This is typical behavior of singlet nitrenes, but not triplet nitrenes, which generally participate in H-atom abstraction reactions to generate radical species. For instance, Espinso et al. (Ibid.) demonstrated that the cyclization of an enantiopure carbamate results in the formation of enantiomerically pure oxazolidinone, wherein one product was observed by chiral GC (Scheme 3).

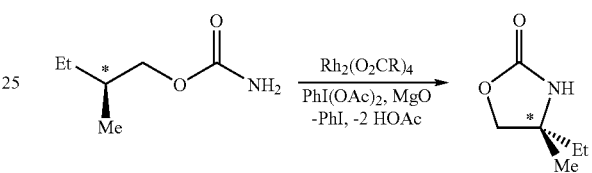

A chiral amination catalyst such as a Ru(II) tetraaryl porphyrin with four chiral auxiliaries on the four aryl rings opened the possibility to inducing enantioselectivity with pro-chiral substrates. See Liang et al. (2004) *J. Org. Chem.*, 69:3610-3619; Liang et al. (2002) *Angew. Chem. Int. Ed.*, 41:3465-3468. For example, when sulfamate esters H$_2$NSO$_3$R were employed, respectable enantioselectivities were observed (Scheme 4)

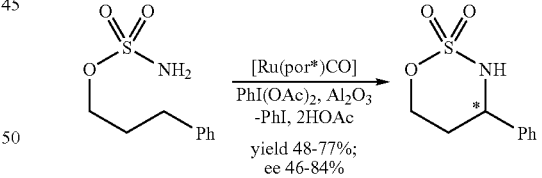

The use of organoazides RN$_3$ could considerably expand the range of amine products that could be obtained through catalytic amination. A cobalt porphyrin system has been reported to aminate toluene and other substrates with benzylic C—H bonds. See Cenini (supra); Caselli et al. (2005) *J. Organometal. Chem.*, 690; Fantauzzi et al. (2005) *Organometallics*, 24:4710-4713; Cenini et al. (1999) *J. Mol. Catal. A*, 137:135-146; Cenini et al. (2000) *Chem. Commun.*, 2265-2266; Ragaini et al (2003) *Chem. Eur. J.*, 9:249-259. Use of p-substituted arylazides X—C$_6$H$_4$N$_3$ (X=NO$_2$, OMe, Cl, H, Me, F, Br, CN) gives rise to the corresponding imine p-XC$_6$H$_4$N=CHPh in 6-38%, whilst amine p-XC$_6$H$_4$NH$_2$ and diazine p-XC$_6$H$_4$N=NC$_6$H$_4$X account for remainder of arylazide (Scheme 5).

Scheme 5.

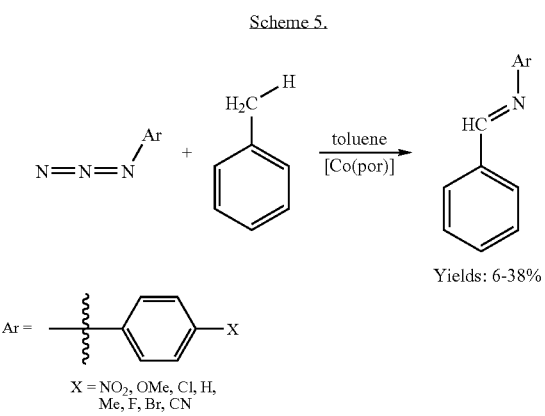

Yields: 6-38%

Substrates with a weaker C—H bond than that of the benzylic position of toluene such as cyclohexene result in the formation of a secondary amine as the predominant product (Scheme 6). For this mode of reactivity, it appears that electron-withdrawing substituents on the aryl ring increase the selectivity towards C—H bond amination.

Scheme 6.

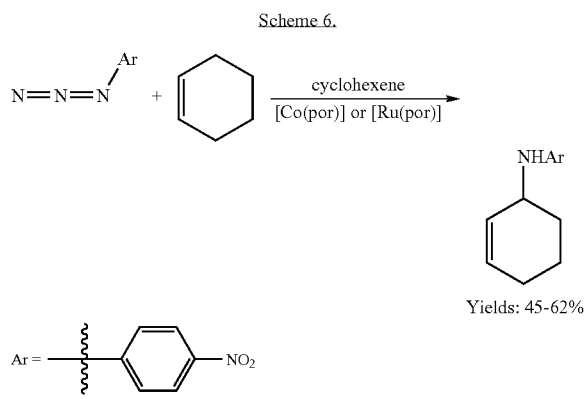

Yields: 45-62%

SUMMARY OF THE INVENTION

Aspects of the present invention relate to a methodology that allows for the use of electron-rich aliphatic azides for amidation of C—H bonds in excellent yields. In certain embodiments, this methodology can be extended for the C—H insertion of any number of nitrenes that can be generated and stabilized by a β-diketiminato metal catalyst. In certain embodiments, said nitrenes may be generated from organoazides, or by oxidation of the corresponding amine.

The present invention described herein employs transition metal (e.g., Cu(I)) complexes of an electron rich, bidentate N,N-donor ligand (β-diketiminate) that reacts with nitrenes to yield a unique metal-nitrene complex, which selectively reacts with hydrocarbons to insert an amine moiety in C—H bonds without many of the problems mentioned above. Aspects of the present invention also relate to olefin aziridination using said β-diketiminato copper catalysts. In addition, the methodology of the present invention can be readily extended to include the stereoselective C—H bond aminations and olefin aziridinatons, and in certain embodiments, may be conducted in an aerobic environment.

Systems of the present invention employ Cu(I) complexes of an electron-rich, bidentate N,N-donor ligand (β-diketiminates) that react with organoazides to promote C—H bond insertion and alkene aziridination. Said reactions may be catalytic in the amount of said complexes.

While existing technology employs environmentally unfriendly oxidants such as $PhI(OAc)_2$ to oxidize an amine $H_2NR$ (generating PhI and 2 equiv. acetic acid) in the presence of a transition metal catalyst to give a nitrene NR active in C—H bond insertion, aspects of the present invention relate to the use of $O_2$ as this oxidant, for which water is the byproduct of oxidation. This avoids the generation of toxic PhI and is far more atom economical.

BRIEF DESCRIPTION OF THE FIGURES

FIG. 10 tabulates the results of reactions between adamantyl azide and various C—H containing substrates catalyzed by $\{[Cl_2NN]Cu\}_2(benzene)$.

FIG. 12 depicts (top) the reaction of $\{[Cl_2NN]Cu\}_2(benzene)$ in benzene with excess dioxygen to give $\{[Cl_2NN]Cu\}_2(\mu\text{-O})_2$ (UV-vis;$\lambda$=344 and 396 nm); and (bottom) the reaction of $\{[Cl_2NN]Cu\}_2(\mu\text{-O})_2$ with a 2,6-disubstituted aniline or ethylbenzene to produce C-H insertion products.

DETAILED DESCRIPTION OF THE INVENTION

Figure 1:
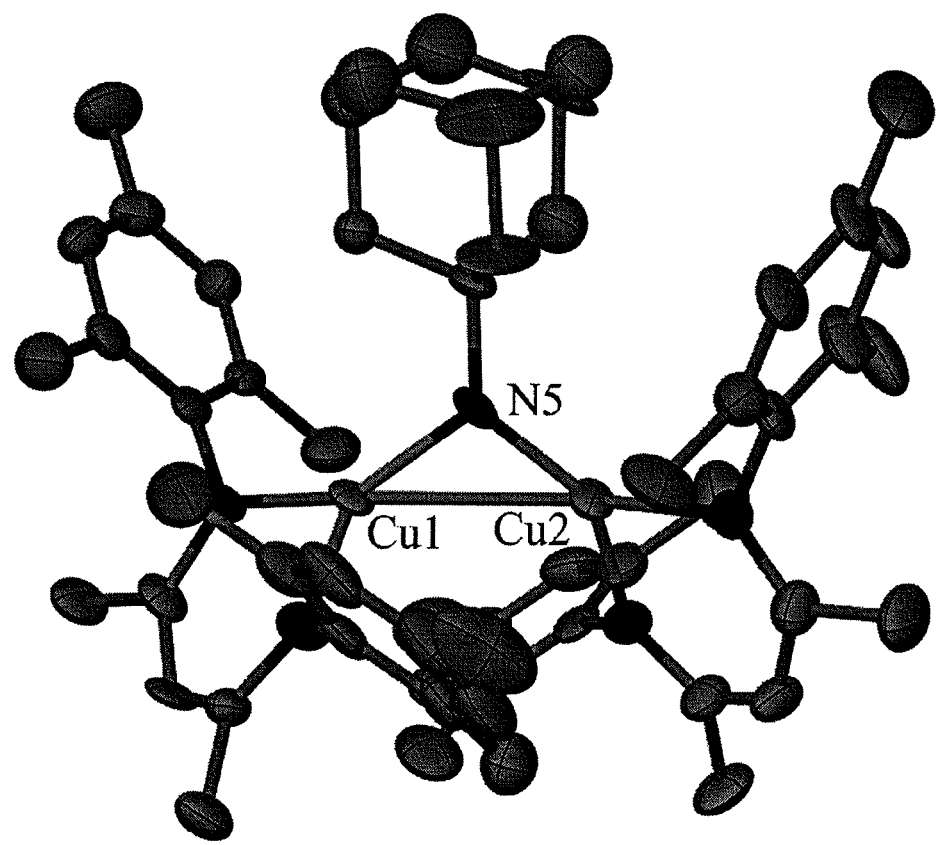
FIG. 1 depicts the X-ray structure of $\{[Me_3NN]Cu\}_2(\mu\text{-NAd})$.

The invention is herein described more fully with reference to the accompanying examples, in which certain preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

The present invention relates generally to β-diketiminato transition metal catalysts and their utility for the catalytic C—H bond insertion of nitrenes; the catalytic amination of C—H bonds with organoazides; the catalytic aziridination of alkenes with organoazides; and the catalytic aerobic amindation of C—H bonds and aziridination of alkenes with amines.

One aspect of the present invention relates to β-diketiminato transition metal compounds. The transition metal can be copper or cobalt. The diketiminato ligand is coordinated to the transition metal atom through two nitrogen atoms bonded to the backbone of the diketiminato ligand. Furthermore, the diketiminato ligand can be optionally substituted with halogens, alkyl groups, or aryl groups. In preferred embodiments, the transition metal is copper and the nitrogen atoms of the diketiminato ligand are substituted with 2,6-dichloro groups. In certain embodiments, the β-diketiminato compound is chiral.

Preparation of Cobalt β-Diketiminato Stabilized Catalysts

Oxo ($O^{2-}$) and imido ($NR^{2-}$) functionalities bound to later first row transition metals attract interest as active agents in atom[1] and group transfer[2] reactions to alkenes as well as in C—H bond functionalization.[3] Due to their important biological roles (especially for Fe),[4] such oxo complexes have commanded considerably more attention than isoelectronic imido counterparts. Despite cobalt's seminal role in synthetic metal-dioxygen chemistry,[5] species bearing oxo functionalities have been established only recently. The bulky tris(pyrazolyl)borates {$^{Me3}$TpCo}$_2$(μ-OH)$_2$ react with $H_2O_2$ to provide {$^{Me3}$TpCo}$_2$(μ-OH)$_2$ species that are susceptible to intramolecular C—H bond abstraction by the oxo ligand.[6,7] {$^{i-PrMe}$TpCo}$_2$(μ-$N_2$) directly reduces $O_2$ by 4 electrons to produce a related, but especially thermally sensitive bis(μ-oxo)dicobalt(III) complex.[7,8] Furthermore, a square-planar Co$^{III}_2$(μ-O)$_2$ species was isolated in the disproportionation of the Co(II) complex [Co($H_2$L)$_2$]$^{2-}$ ($H_2$L=bis[(t-butyl)aminocarbonyl]-1,2-diamidoethane) in the presence of $O_2$.[9] Imido functionalities bound to later first row metals are beginning to exhibit reactivity patterns reminiscent of oxo species. For instance, Theopold observed intramolecular C—H bond abstraction by inferred Tp"Co≡NTMS intermediates in the reaction of Tp"Co($N_2$) with $N_3$TMS.[10] Peters has shown that tris(phosphino)borate complexes [$P_3$B]M≡N(p-tolyl) (M=Fe,[11a] Co[11b]) undergo imido group transfer to CO providing p-tolylNCO. Exploring relationships between oxo and imido functionalities in later, first row chemistry, we describe herein the synthesis of a β-diketiminato Co(I) arene adduct and its reactivity with dioxygen, organoazides, and a nitrosobenzene to provide a family of structurally diverse oxo and imido complexes.[12]

The paramagnetic, tetrahedral Co(II) β-diketiminate[13] [Me$_2$NN]Co(I)(2,4-lutidine) may be prepared in 90% yield from reaction of Tl[Me$_2$NN][14] with CoI$_2$(2,4-lutidine)$_2$ as teal crystals. Reduction of this species with Mg powder in toluene provides air-sensitive, red crystals of [Me$_2$NN]Co (η$^6$-toluene) in 60-70% yield on a gram scale (Scheme 7). This $d^8$ Co(I)-arene adduct is high-spin as evidenced by its room temperature magnetic moment of 2.7 B.M. in toluene-$d_8$. While diamagnetic [Me$_2$NN]Rh(arene) and {[Me$_2$NN]Rh}$_2$(arene) complexes favor η$^4$-arene coordination,[15] the X-ray structure of 1 reveals an η$^6$-toluene ligand (Co—C=2.207(6)–2.288(5)Å) bound to the [Me$_2$NN]Co fragment (Scheme 7).

Scheme 7 depicts the synthesis, structure, and reactivity of 1. Addition of several equivalents of dry oxygen to 1 in ether at room temperature results in an immediate color change from red to violet signaling the formation of {[Me$_2$NN]Co}$_2$ (μ-O)$_2$ (2) that may be isolated in 75% yield as maroon crystals (Scheme 7). The X-ray structure of 2 obtained at –90° C. consists of two [Me$_2$NN]Co fragments related by inversion separated by 2.716(4) Å. Final refinement suggested positional disorder for the bridging oxygen atoms. The predominant orientation (86% occupancy) consists of oxo atoms related by inversion that appear in roughly square planar sites[9] (22.2° and 23.0° twist angles between the N—Co—N and O1-Co—O1' planes) with nearly identical Co—O1 and Co—O1' bond distances of 1.784(3) and 1.793(4) Å. The minor orientation consists of two inequivalent oxo atoms that symmetrically bridge in a tetrahedral disposition and exhibit somewhat lengthened Co—O distances. The short metal-metal and metal-oxo distances found in 2 compare favorably to those in related "diamond core" $M_2$(μ-O)$_2$ (M=Fe—Cu) structures.[3c,9]

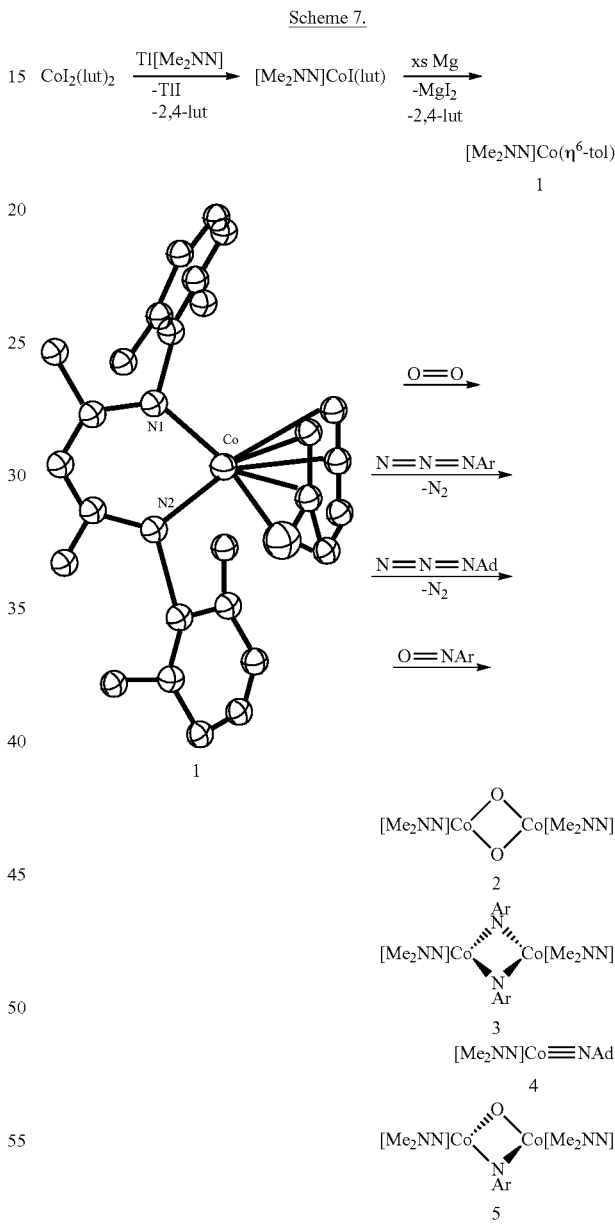

Scheme 7.

While toluene-$d_8$ solutions of 2 exhibit sharp $^1$H NMR signals from –75 to +80° C., the β-diketiminate resonances become contact shifted toward higher field with increasing temperature. For instance, the backbone C—H and Ar-Me resonances shift from δ 6.1 and 0.5 ppm to δ –3.5 and –3.0 ppm, respectively. Over this temperature range, the solution magnetic moment of 2 in toluene-$d_8$ increases from 3.9 to 4.3 B.M. This reversible behavior suggests that the $d^6$ Co(III)

centers in 2 are antiferromagnetically coupled; a detailed magnetic investigation of 2 is underway.

Aiming to prepare related imido complexes, we explored the reactivity of 1 with organoazides. Reaction of [Me$_2$NN]Co($\eta^6$-toluene) with N$_3$Ar (Ar=3,5-Me$_2$C$_6$H$_3$) in ether results in rapid effervescence and formation of the tetrahedral Co(III)-imido bridged dimer {[Me$_2$NN]Co}$_2$($\mu$-NAr)$_2$ (3). Its solution magnetic moment of 8.8 B.M. in benzene-d$_6$ at RT indicates the presence of two fully high-spin, ferromagnetically coupled d$^6$ centers. The X-ray structure of 3 exhibits a considerably longer Co—Co separation (3.067(3) Å) than found in 2 with Co—N(imido) bond distances of 1.983(3) and 1.988(3) Å. In contrast, reaction of 1 with the more sterically demanding N$_3$Ad (Ad=1-adamantyl) leads to the formation of the three-coordinate terminal imide [Me$_2$NN]Co=NAd (5) that may be isolated in 50% yield as red crystals. The X-ray structure of 5 reveals a Co—N(imide) bond distance of 1.624(4) Å which is at the short end of the range 1.64-1.70 Å observed in sparse examples of Fe,[11,16] Co,[12] and Ni[17] terminal imides. Though in the solid state the imido substituent is somewhat bent (Co—N3-C22=161.5(3)°) toward the opposite side of the trigonal plane formed by the three N-donors from which the Co center is slightly (0.169 Å) displaced, diamagnetic 4 exhibits C$_{2v}$-symmetric $^1$H and $^{13}$C NMR spectra in benzene-d$_6$ at RT. This low-spin d$^6$ configuration in 4 would allow $\pi$-donation of the two orthogonal lone pairs of an sp-hybridized imido N-atom into two empty metal d orbitals destabilized by $\sigma$- and $\pi$-interactions with the $\beta$-diketiminate N-donor atoms. Preliminary DFT calculations support this simple orbital picture that predicts considerable metal-imido multiple bond character in 4 and allows its formulation as a 16-electron species.

To explore the generality of 1 as a precursor to oxo and imido species via reductive cleavage of double bonds to O and N, we exposed 1 to 0.5 equiv. of O=NAr (Ar=3,5-Me$_2$C$_6$H$_3$) in ether which results in the formation of the binuclear {[Me$_2$NN]Co}$_2$($\mu$-O)($\mu$-NAr) (5) in 33% isolated yield. This 4 electron reduction of a nitrosobenzene stands in contrast to the reaction of the related CpCo(C$_2$H$_4$)$_2$ with O=NPh which leads to [CpCo]$_2$($\mu$-$\eta^2$:$\eta^1$-PhNO)$_2$.[18] The X-ray structure of 5 is intermediate between the structures observed for the square-planar bis($\mu$-oxo) 2 and tetrahedral bis($\mu$-imido) 3 with opposing [Me$_2$NN]Co fragments that are nearly orthogonal (89.2° twist angle). While the Co—Co separation (2.7420(6) Å) and Co—O distances (1.783(2) and 1.786(2) Å) in 5 are similar to those found in the square planar bis($\mu$-oxo) 2, the Co—N distances (1.821(3) and 1.823(3) Å) lie between those in the tetrahedral bis($\mu$-imido) 3 and terminal imido 4. Furthermore, 5 possesses a non-temperature dependent solution magnetic moment of 4.9 B.M. that falls between that observed for 2 and 3.

In summary, [Me$_2$NN]Co($\eta^6$-toluene) serves as a synthon to the 12-electron, two-coordinate [Me$_2$NN]Co fragment that cleaves O=O, N=N, and O=N bonds to provide a family of structurally diverse Co(III) oxo and imido species. Subsequent reports will detail their magnetic behavior and reactivity patterns. For instance, the M=NR bond of terminal 4 undergoes ready cycloaddition reactions with organoazides and isocyanates. Given the thermal stability of both bis($\mu$-oxo) 2 and terminal imido 4, a monomeric Co(III) oxo complex may be a viable synthetic target. Also see Example 12.

REFERENCES FOR PREPARATION OF COBALT β-DIKETIMINATO STABILIZED CATALYSTS (1) (a) Palucki, M.; Finney, N. S.; Pospisil, P. J.; Güler, M. L.; Ishida, T.; Jacobsen, E. N. J. Am. Chem. Soc. 1998, 120, 948. (b) Groves, J. T.; Lee, J.; Marla, S. S. J. Am. Chem. Soc. 1997, 119, 6269. (c) Collman, J. P.; Wang, Z.; Straumanis, A.; Quelquejeu, M. J. Am. Chem. Soc. 1999, 121, 460. (d) Feichtinger, D.; Plattner, D. A. Chem. Eur. J. 2001, 7, 591.

(2) (a) Groves, J. T.; Takahashi, T. J. Am. Chem. Soc. 1983, 105, 2073. (b) DuBois, J. L.; Tomooka, C. S.; Hong, J.; Carreira, E. M. Acc. Chem. Res. 1997, 30, 364. (c) Li, Z.; Quan, R. W.; Jacobsen, E. N. J. Am. Chem. Soc. 1995, 117, 5889. (d) Brandt, P.; Sodergren, M. J.; Andersson, P. G.; Norrby, P.-O. J. Am. Chem. Soc. 2000, 122, 8013. (e) Au, S.-M.; Huang, J.-S.; Yu, W.-Y.; Fung, W.-H.; Chi, C.-M. J. Am. Chem. Soc. 1999, 121, 9120. (f) Wigley, D. E. Prog. Inorg. Chem. 1994, 42, 239. (g) Mansuy, D.; Mahy, J.-P.; Dureault, A.; Bedi, G.; Battioni, P. J. Chem. Soc., Chem. Commun. 1984, 1161.

(3) (a) Chen, K.; L Que, J. J. Am. Chem. Soc. 2001, 123, 6327. (b) Collman, J. P.; Chien, A. S.; Eberspacher, T. A.; Brauman, J. I. J. Am. Chem. Soc. 1998, 120, 425. (c) Que, Jr., L.; Tolman, W. B. Angew. Chem. Int. Ed. 2002, 41, 1114-1137 and references within.

(4) (a) Sono, M.; Roach, M. P.; Coulter, E. D.; Dawson, J. H. Chem. Rev. 1996, 96, 2841. (b) Solomon, E. I.; Brunold, T. C.; Davis, M. I.; Kemsley, J. N.; Lee, S.-K.; Lehnert, N.; Neese, F.; Skulan, A. J.; Yang, Y.-S.; Zhou, J. Chem. Rev. 2000, 100, 235. (c) Cyclochrome P-450: Structure, Mechanism, and Biochemistry; de Montellano, P. R. O., Ed.; Plenum: New York, 1985. (d) Manchanda, R.; Brudvig, G. W.; Crabtree, R. H. Coord. Chem. Rev. 1995, 144, 1. (e) Feig, A. L.; Lippard, S. J. Chem. Rev. 1994, 94, 759.

(5) Bianchini, C.; Zoellner, R. W. Adv. Inorg. Chem. 1996, 44, 263.

(6) (a) Hikichi, S.; Akita, M.; Moro-oka, Y. Coord. Chem. Rev. 2000, 198, 61. (b) Hikichi, S.; Yoshizawa, M.; Sasakura, Y.; Akita, M.; Moro-oka, Y. J. Am. Chem. Soc. 1998, 120, 10567.

(7) Hikichi, S.; Yoshizawa, M.; Sasakura, Y.; Komatsuzaki, H.; Moro-oka, Y.; Akita, M. Chem. Eur. J. 2001, 7, 5012.

(8) (a) Reinaud, O. M.; Theopold, K. H. J. Am. Chem. Soc. 1994, 116, 6979. (b) Theopold, K. H.; Reinaud, O. M.; Doren, D.; Konecny, R. In 3rd World Congress on Oxidation Catalysis; Grasselli, R. K., Oyama, S. T., Gaffney, A. M., Lyons, J. E., Eds.; Elsevier: Amsterdam, 1997, p 1081.

(9) Larsen, P. L.; Parolin, T. J.; Powell, D. R.; Hendrich, M. P.; Borovik, A. S. Angew. Chem. Int. Ed. 2003, 42, 85.

(10) Thyagarajan, S.; Shay, D. T.; Incarvito, C. D.; Rheingold, A. L.; Theopold, K. H. J. Am. Chem. Soc. 2003, 125, 4440.

(11) (a) Brown, S. D.; Betley, T. A.; Peters, J. C. J. Am. Chem. Soc. 2003, 125, 322. (b) Jenkins, D. M.; Betley, T. A.; Peters, J. C. J. Am. Chem. Soc. 2002, 124, 11238.

(12) Some of this work has been presented: Dai, X.; Warren, T. H., Abstracts of Papers, 224th National Meeting of the American Chemical Society, Boston, Mass., Aug. 18-22, 2001, No. INOR 407.

(13) Related, bulkier three- and four-coordinate Co(II) b-diketiminates have been recently reported: Holland, P. L.; Cundari, T. R.; Perez, L. L.; Eckert, N. A.; Lachicotte, R. J. J. Am. Chem. Soc. 2002, 124, 14416.

(14) Dai, X.; Warren, T. H. Chem. Commun. 2001, 1998.

(15) Budzelaar, P. H. M.; Moonen, N. N. P.; de Gelder, R.; Smits, J. M. M.; Gal, A. W. Chem. Eur. J. 2000, 6, 2740.

(16) Verma, A. K.; Nazif, T. N.; Achim, C.; Lee, S. C. J. Am. Chem. Soc. 2000, 122, 11013.

(17) (a) Mindiola, D. J.; Hillhouse, G. L. J. Am. Chem. Soc. 2001, 123, 4623. (b) Kogut, E.; Wiencko, H. L.; Zhang, L.; Warren, T. H. manuscript in preparation.
(18) Stella, S.; Floriani, C.; Chiesi-Villa, A.; Guastini, C. J. Chem. Soc., Dalton Trans. 1988, 545.

β-Diketiminato and Anilidoimine Copper Nitrenes: Stoichiometric Nitrene C—H Bond Insertion Aspects of the present invention relate to stoichiometric nitrene C—H bond insertion with β-diketiminato and anilidoimine copper nitrenes.

Dicopper nitrenes {[Me$_3$NN]Cu}$_2$(μ-NAr), [Me$_3$NN]Cu(μ-NAr)Cu[Me$_2$AI], and {[Me$_2$AI]Cu}$_2$(μ-NAr)(wherein Ar=3,5-Me$_2$C$_6$H$_3$) have been synthesized and isolated. See Badiei et al. (2006) *JACS*, 128:15056-15057. Terminal nitrene intermediates [Cu]=NAr are thought to be present in these solutions as a result of dissociation of a copper fragment [Cu] from the dicopper nitrenes [Cu]$_2$(μ-NAr), as suggested by crossover experiments. The extent of dissociation is low—no terminal nitrene species can be seen by $^1$H NMR spectroscopy in benzene-d$_6$ solution at room temperature.

These dicopper nitrenes undergo stoichiometric nitrene transfer reactivity with nucleophiles such as PMe$_3$ and CNBu$^t$ to give ArN=PMe$_3$ and ArN=C=NBu$^t$ in greater than 90% yield. In the absence of any added substrate, benzene-d$_6$ solutions of the copper nitrenes decompose to give the diazene ArN=NAr as the predominant nitrene-containing species. Some amine H$_2$NAr and hydrazine ArNHNHAr is also observed, suggesting that H-atom abstraction from C—H bonds of the ligand may be taking place—abstraction from the solvent would give D$_2$NAr and ArNDNDAr.

The use of an electron-rich adamantyl nitrene substituent gives rise to significantly more reactive copper nitrenes. Reaction of {[Me$_3$NN]Cu}$_2$(μ-toluene) with N$_3$Ad in ether allows for the isolation of the green {[Me$_3$NN]Cu}$_2$(μ-NAd) in reasonable yield. The X-ray structure of {[Me$_3$NN]Cu}$_2$(μ-NAd) is similar to that reported for {[Me$_3$NN]Cu}$_2$(μ-NAr), with bridging of the NAd ligand between two Cu centers separated by 2.900(2) Å and Cu—N distances of 1.782(6) and 1.823(5) Å (see FIG. 1). This adamantyl nitrene is significantly less stable than its aryl counterpart; recrystallization led to the isolation of a red crystalline material which gave an elemental analysis consistent with the composition expected for [Me$_3$NN]Cu=NAd. Nonetheless, it is believed that this is isomer derived from the insertion of the NAd moiety into one of the N-aryl o-C—H bonds, rather than the terminal nitrene.

Preparation of the species [Me$_2$NN$_B$]Cu(η$^2$-CH$_2$CHBu$^t$), which has t-butyl groups on the backbone, is detailed in Scheme 8 below.

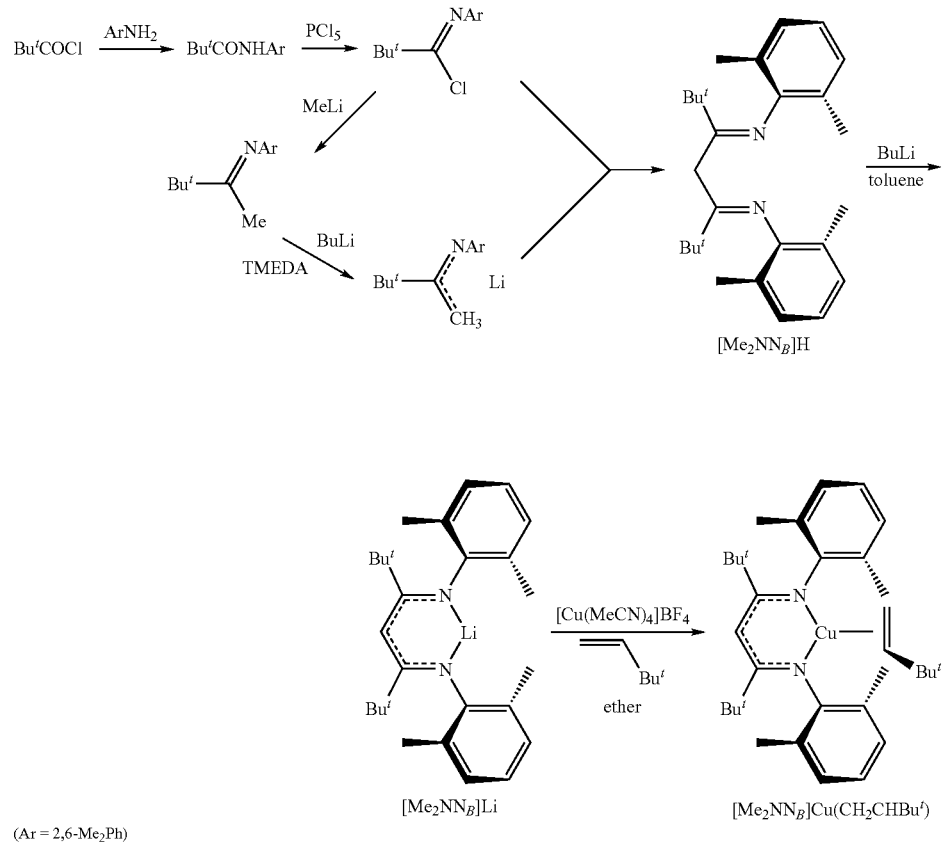

(Ar = 2,6-Me$_2$Ph)

Figure 2:
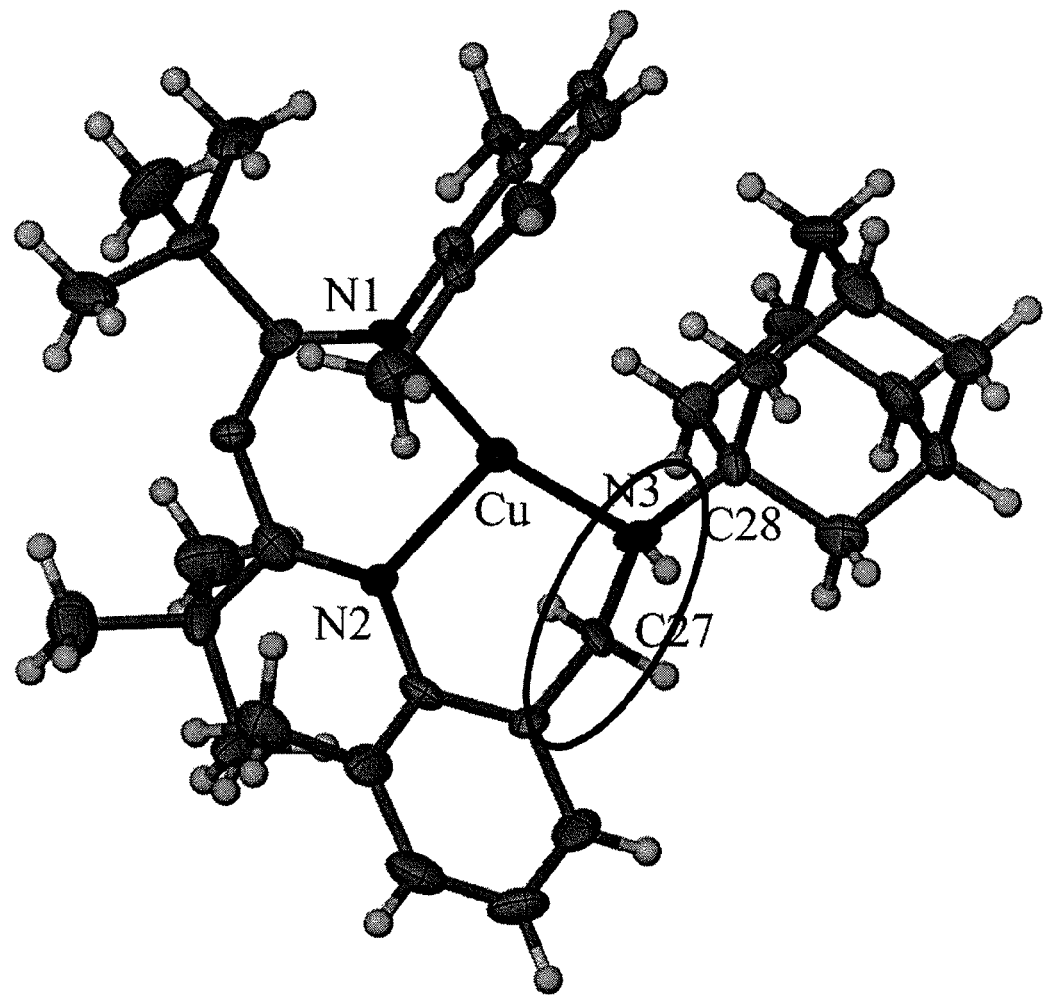
FIG. 2 depicts the X-ray structure of Cu(I) β-diketiminato amine product 6, which was isolated from the C—H insertion reaction of $[Me_2NN_B]Cu(\eta^2\text{-}CH_2CHBu^t)$ with $N_3Ad$; coordination of the $ArCH_2$—NHAd functionality is highlighted.

Reaction of [Me$_2$NN$_B$]Cu(η$^2$-CH$_2$CHBu$^t$) with N$_3$Ad leads to the isolation of the Cu(I) β-diketiminato amine 6 in which a NAd moiety has inserted into one of the N-aryl o-CH$_2$—H bonds (Scheme 9). The X-ray crystal structure (FIG. 2) shows coordination of the ArCH$_2$—NHAd functionality and confirms that the nitrene moiety inserted into a benzylic C—H bond of the one of the four N-aryl o-Me groups.

Scheme 9.

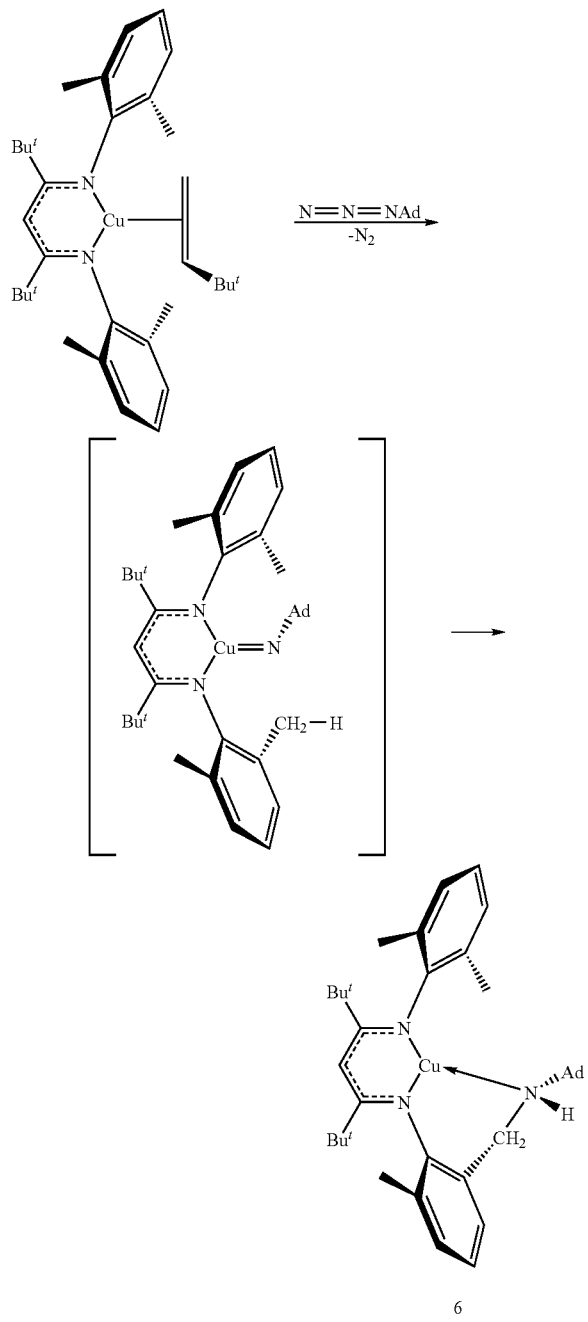

New Catalyst Development: Catalytic Insertion of Nitrenes into C—H Bonds

Aspects of the present invention relate to the development of a novel β-diketiminato catalysts and their utility for insertion of nitrenes in C—H bonds.

Figure 3:
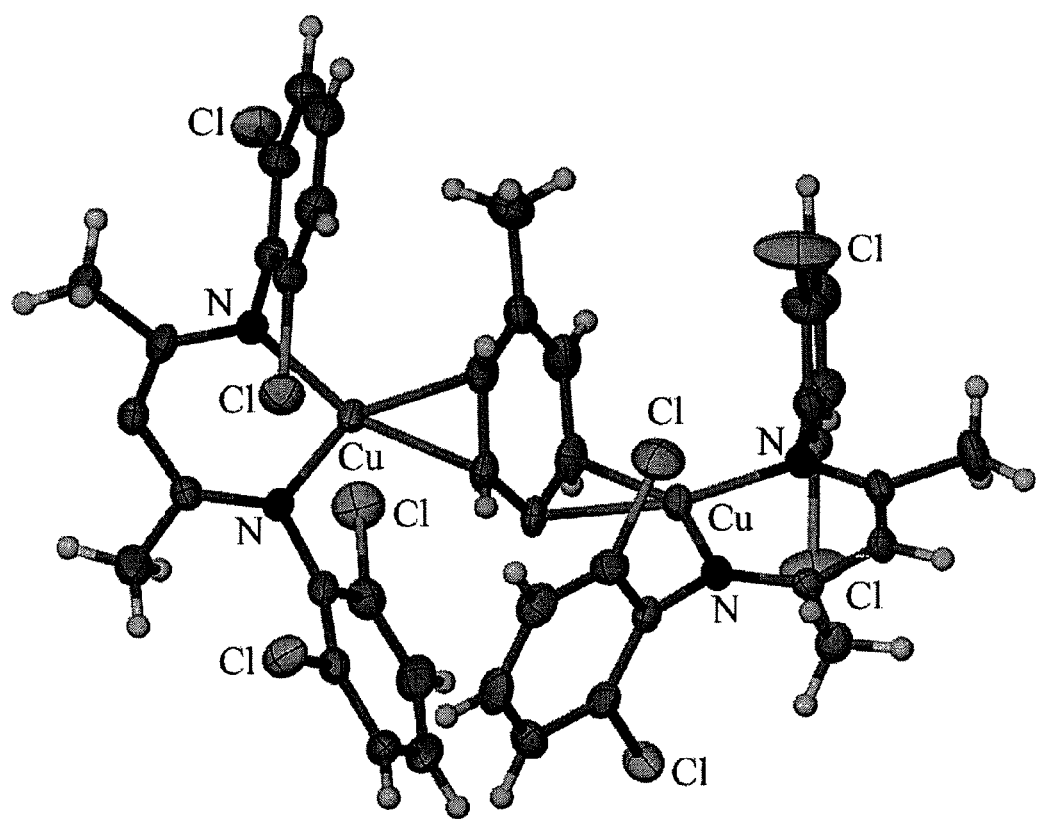
FIG. 3 depicts the X-ray structure of $\{[Cl_2NN]Cu\}_2(\mu\text{-toluene})$ 7.

Following the results described above, it was reasoned that the use of substituents in the o-Ar positions, which would be inert to the extremely reactive Cu=NR functionality, could result in the insertion of the nitrene into exogenous C—H bonds. For example, Cl atoms were substituted for the Me groups in the o-positions of the N-aryl rings of the species reported above. Thus, the new product {[Cl$_2$NN]Cu}$_2$(μ-toluene) (7) can be prepared in high yield from the reaction of free diimine H[Cl$_2$NN] and CuOBu$^t$ in toluene in 94% yield (Scheme 10). FIG. 3 depicts the X-ray structure of {[Cl$_2$NN]Cu}$_2$(μ-toluene) 7. Also see Example 1.

Scheme 10.

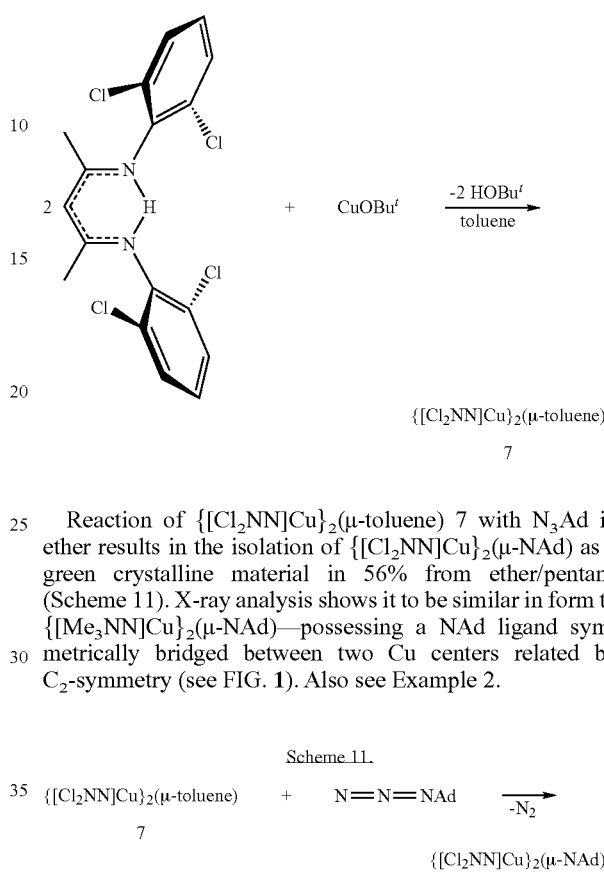

Reaction of {[Cl$_2$NN]Cu}$_2$(μ-toluene) 7 with N$_3$Ad in ether results in the isolation of {[Cl$_2$NN]Cu}$_2$(μ-NAd) as a green crystalline material in 56% from ether/pentane (Scheme 11). X-ray analysis shows it to be similar in form to {[Me$_3$NN]Cu}$_2$(μ-NAd)—possessing a NAd ligand symmetrically bridged between two Cu centers related by C$_2$-symmetry (see FIG. 1). Also see Example 2.

Scheme 11.

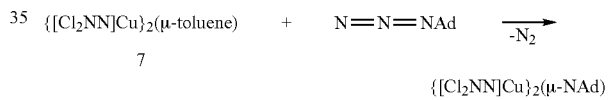

Figure 4:
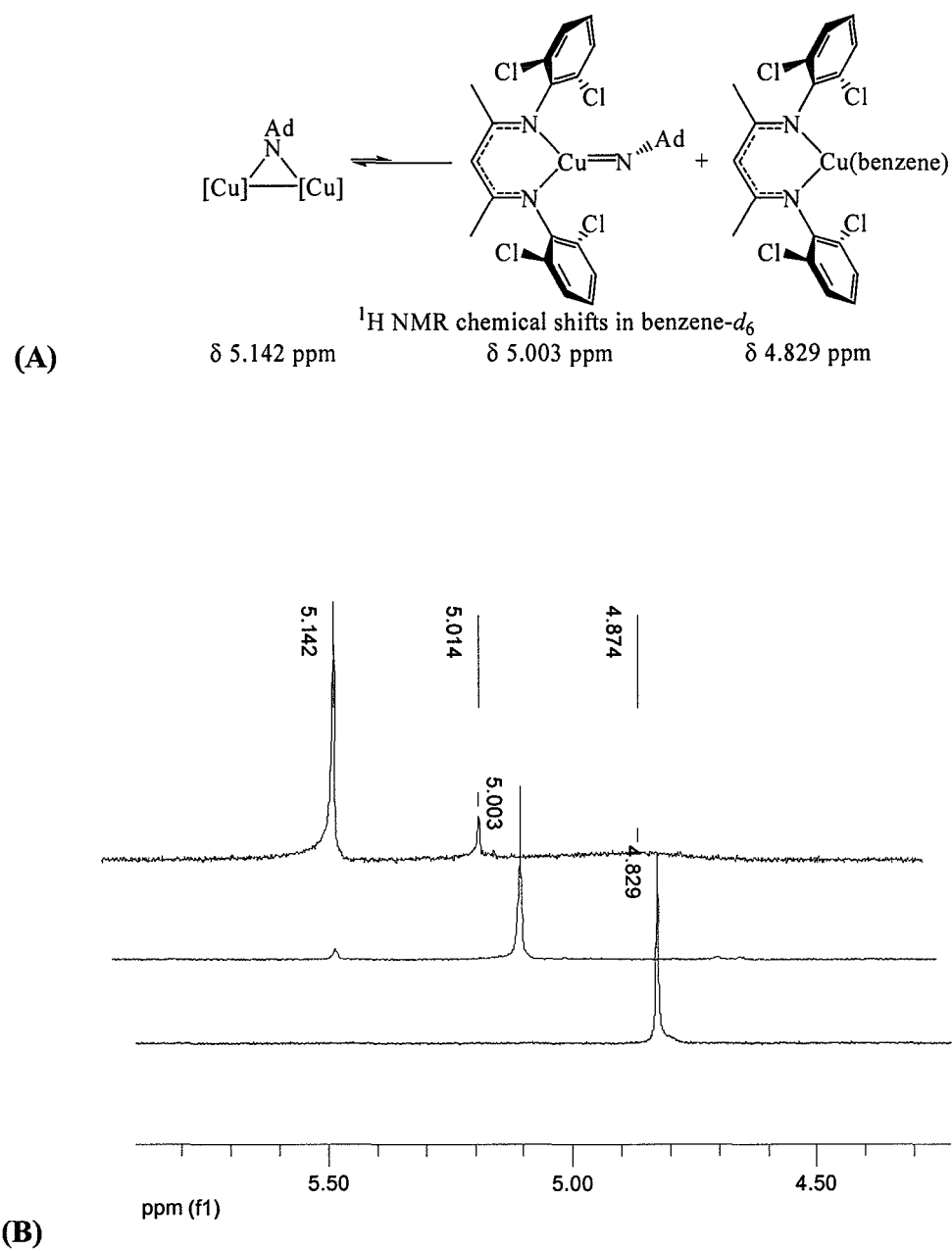
FIG. 4 depicts $^1H$ NMR analysis of the chemical shifts for a solution of $\{[Cl_2NN]Cu\}_2(\mu\text{-NAr})$ in benzene-$d_6$: (A) reaction scheme; (B)$^1H$ NMR spectra (300 MHz, benzene-$d_6$) of C—H backbone of (from top to bottom): dicopper nitrene $\{[Cl_2NN]Cu\}_2(\mu\text{-NAd})$, terminal nitrene species $[Cl_2NN]Cu{=}NAd$ generated after prolonged heating, and $^1H$ NMR of pure $[Cl_2NN]Cu(arene)$.

FIG. 4 depicts $^1$H NMR analysis of the chemical shifts for a solution of {[Cl$_2$NN]Cu}$_2$(μ-NAr) in benzene-d$_6$: (A) reaction scheme; (B) $^1$H NMR spectra. Benzene-d$_6$ solutions of {[Cl$_2$NN]Cu}$_2$(μ-NAr) show one major backbone C—H peak at δ 5.142 ppm, as well as a triplet for the p-Ar position. Two other β-diketiminato backbone resonances at δ 5.003 and 4.829 ppm are always observed in benzene-d$_6$ solutions of {[Cl$_2$NN]Cu}$_2$(μ-NAr). The resonance at δ 4.829 ppm is [Cl$_2$NN]Cu(benzene-d$_6$), suggesting that the other resonance at δ 5.003 ppm is [Cl$_2$NN]Cu=NAd. See also Example 6.

The observation of the terminal nitrene [Cl$_2$NN]Cu=NAd by $^1$H NMR spectroscopy in the normal chemical shift region indicates that it is likely a singlet species (S=0). This equilibrium is similar to that observed for the dissociation of the dicopper carbene {[Me$_x$NN]Cu}$_2$(μ-CPh$_2$)(x=2 or 3) into the terminal carbene [Me$_x$NN]Cu=CPh$_2$ and the β-diketiminato Cu(I) arene adduct [Me$_x$NN]Cu(arene). See Dai, X. and Warren, T. H. (2004) JACS, 126:ASAP; Badiei, Y. M. and Warren, T. H. (2005) J. Organomet. Chem., 690:5989-6000.

The new dicopper nitrene {[Cl$_2$NN]Cu}$_2$(μ-NAr) undergoes stoichiometric reaction with hydrocarbons such as toluene and cyclohexane to insert the NAd moiety into C—H bonds to form PhCH$_2$NHAd and CyNHAd, respectively, in good yields along with the generation of the [Cl$_2$NN]Cu fragment. The use of N-aryl o-Cl substituents thus appears to render the copper(I) β-diketiminato fragment [Cl$_2$NN]Cu stable towards to extremely reactive [Cu]=NAd functionality.

Steric bulk n the catalyst will tend to prevent nitrene dimerization. If the β-diketiminato ligand structure of intermediates [Cu]=NR is appropriately selected so that the formation of a [Cu](μ-RN=NR)[Cu] is not possible, nitrene dimerization should be shut down. This motivates the construction of sterically bulky β-diketiminates as shown below. Molecular models suggest that a dimerization reaction would not be sterically possible in such a system.

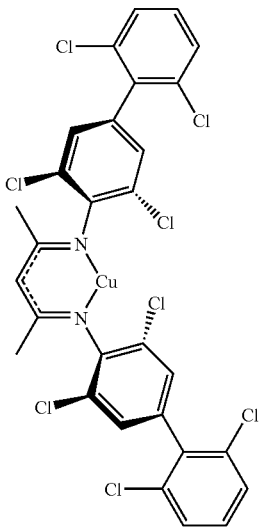

Scope of Organoazide Substrates

In certain embodiments, tertiary azides are the most successful substrates. In certain embodiments, primary (and presumably secondary) alkyl azides undergo a rearrangement [Cu]=NCHR→[Cu](NH=CR) which appears faster than most inter- or intramolecular reactions with C—H bonds. Nevertheless, we have shown that arylazides are appropriate substrates for C—H insertion reactions. There can be diazene (ArN=NAr) byproduct formed in this reaction, which results from the coupling of two [Cu]=NAr intermediates.

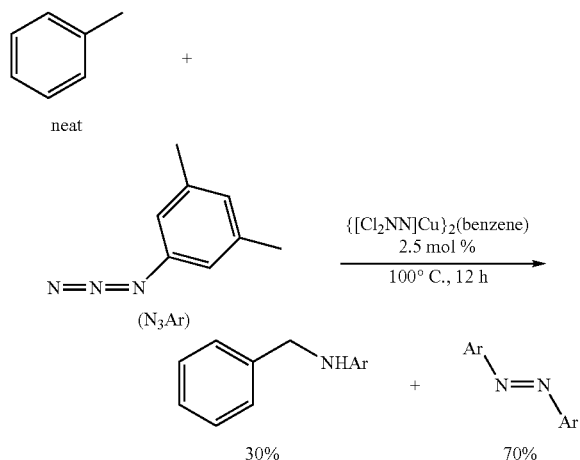

A particularly interesting class of substrates are α-azido esters $N_3CMe_2C(O)OR$ which are easily prepared from the corresponding α-bromo esters $BrCMe_2C(O)OR$, many of which are commercially available. These substrates will enable the formation of N-alkyl amino esters in intermolecular reactions and 5-oxazolidinones or morpholin-2-ones in intramolecular reactions, depending on the relative ability to form 5- and 6-membered rings.

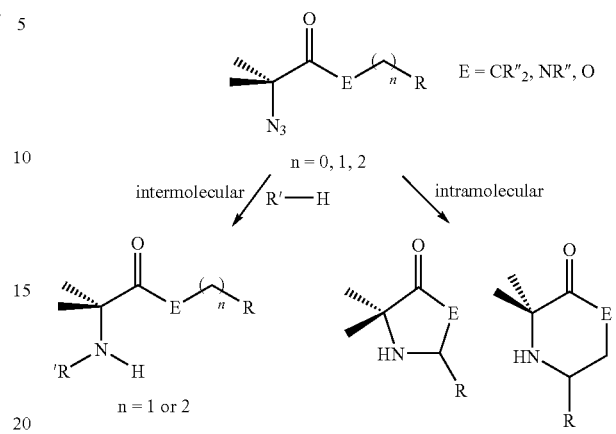

Catalytic Amination of C—H Bonds with Organoazides

Aspects of the present invention relate to catalytic amination of C—H bonds with organoazides. In certain embodiments, the [Cl$_2$NN]Cu fragment serves as a competent catalyst for the amination of toluene and cyclohexane. N$_3$Ad is converted to PhCH$_2$NHAd in 95% yield when heated to 110° C. for 3 h in neat toluene in the presence of 10 mol % {[Cl$_2$NN]Cu}$_2$(μ-toluene) 7. The remainder is the imine PhCH=NAd in 5% yield from secondary reaction of PhCH$_2$NHAd with a subsequent equivalent of N$_3$Ad (Scheme 12).

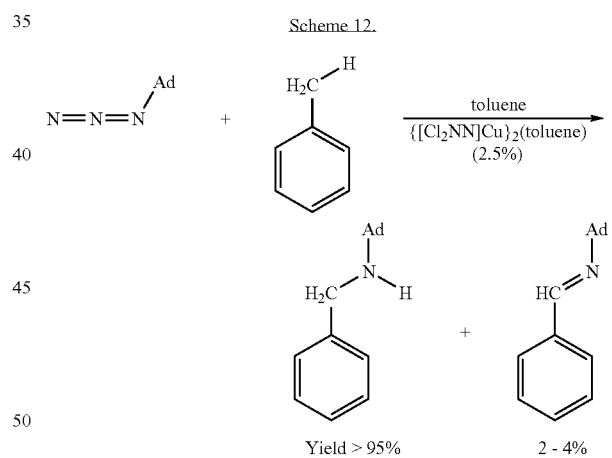

Catalytic amination of cyclohexane also takes place in neat cyclohexane at 110° C. over two days to give the amine CyNHAd in ca. 80% yield. In contrast to the more easily oxidized benzyl amine, no secondary product was observed (Scheme 13).

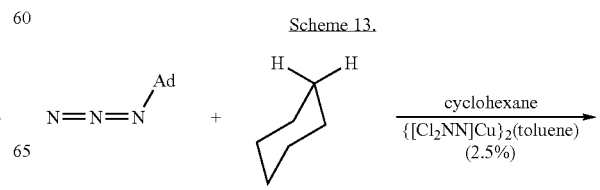

-continued

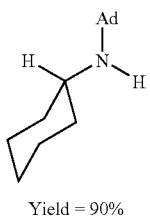

Yield = 90%

In certain embodiments, the reaction times of these reactions can be considerably decreased with the assistance of a microwave reactor. In certain embodiments, the conditions employed in a microwave reactor are 110° C., 1 hour, neat substrate. See also Example 5.

Scheme 14.

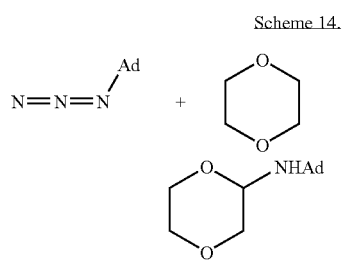

Other azides may also be employed. In another embodiment, the use of trimethylsilyl azide (TMSN$_3$) in toluene with 5 mol % {[Cl$_2$NN]Cu}$_2$(μ-toluene) at 110° C. over 2 days results in the detection of a species consistent with PhCH$_2$NHTMS. Similarly, TsN$_3$ also gives rise to the amination product PhCH$_2$NHTs, also in lower yield.

In certain embodiments, secondary and primary azides N$_3$R may be tolerated (e.g., CyN$_3$ and PhCH$_2$N$_3$). It is possible that the nitrene intermediate [Cu]=NCHR$^1$R$^2$ may not be stable towards rearrangement to the imines [Cu] (HN=CR$^1$R$^2$) under conditions required for catalytic amination.

In certain embodiments, the novel catalyst systems of the present invention are also applicable to the class of substrates organoazides, RCON$_3$, wherein the azido functionality is attached to a carbonyl group. Many such organoazides (RCON$_3$) are susceptible to a thermal Curtius rearrangement to give the corresponding isocyanate RNCO (Scheme 15). This rearrangement can proceed either in concert with N$_2$ loss or from a nitrene intermediate RCON following N$_2$ loss. See Liu et al (2004) *J. Org. Chem.*, 69:8583-8593; L'Abbé, G. (1969) *Chem. Rev.*, 69:345-363.

Scheme 15.

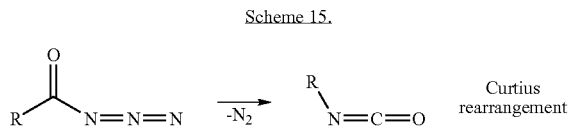

Flash photolysis of carbonyl azides RCON$_3$ has been used to generate singlet nitrene intermediates capable of C—H bond insertion, even though the triplet state of many of these nitrenes is thermodynamically favored (Scheme 16). See Lwoswski, W. and Linke, S (1977) *Liebigs Ann. Chem.*, 8-19. Under appropriate photochemical protocols, intramolecular C—H insertion into aliphatic C—H bonds may take place.

Scheme 16.

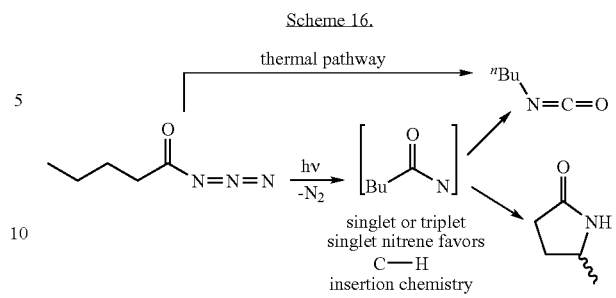

Thermal intramolecular variants of this reaction are known in which new N—C(aryl) bonds are made (Scheme 17). See Pampín et al. (2002) *Tetrahedron Lett*, 43:4551-4553; Rajakumar, P. and Srisailas, M. (2004) *Synth. Commun.*, 34:1811-1818.

Scheme 17.

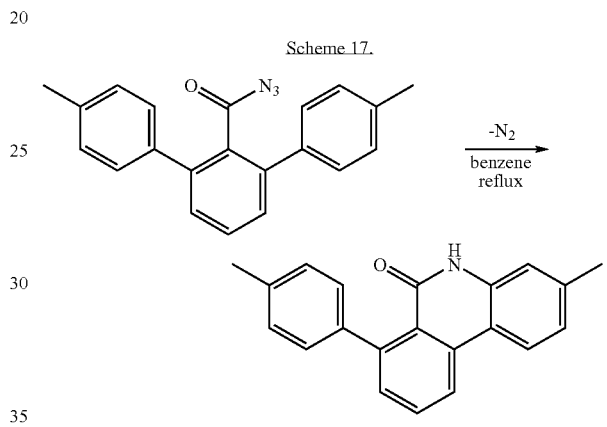

Experiments with novel catalyst systems of the present invention demonstrate that N$_2$ is rapidly expelled from PhC(O)N$_3$ upon reaction with 2.5 mol % {[Cl$_2$NN]Cu}$_2$(μ-toluene) in toluene, and that the intermolecular insertion product PhC(O)NHCH$_2$Ph is observed by GC/MS (Scheme 18). This demonstrates that species with reactivity patterns consistent with singlet nitrenes can be generated under non-photochemical conditions by use of copper catalyst systems in certain embodiments of the present invention.

Scheme 18.

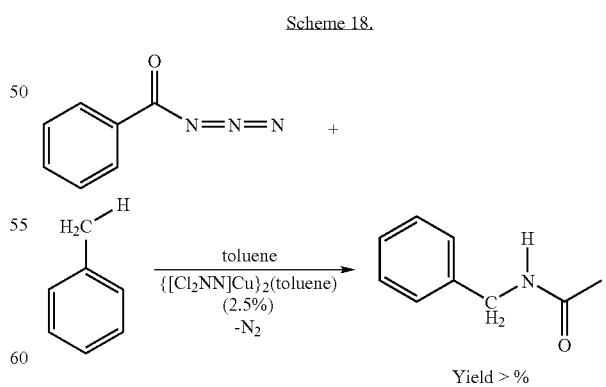

Yield > %

In certain embodiments, an intramolecular variant of this reaction is generated when $^n$BuCON$_3$ is added to 5 mol % {[Cl$_2$NN]Cu}$_2$(μ-toluene) in toluene. In accord with other nitrenes generated, the cyclic lactam is the expected product (Scheme 19).

Scheme 19.

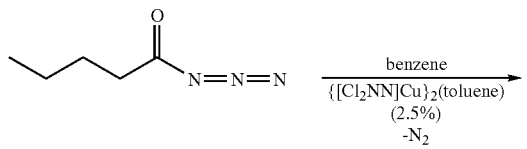

In certain embodiments, aspects of the present invention may also be selective for 5 and/or 6 membered rings (Scheme 20).

Scheme 20.

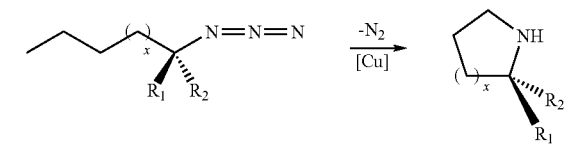

x = 1, 2, 3...
Wherein [Cu] is a copper catalyst system of the present invention.

The order of reactivity of the metal nitrene catalyst species would be predicted to be fastest with tertiary C—H bonds, and slowest with primary C—H bonds used to form lactams and other 5- and 6-membered N-containing heterocycles. A green solution characteristic of dicopper nitrenes [Cu]$_2$(m-NR) is generated when $^n$BuCON$_3$ is added to 5 mol % {[Cl$_2$NN]Cu}$_2$(m-toluene) in toluene.

In certain embodiments, the use of a chiral version of the catalyst could lead to the formation of chiral heterocycles. The presence of singlet nitrene intermediates gives the expectation of retention of stereochemistry during insertion into C—H bonds (Scheme 21).

Scheme 21.

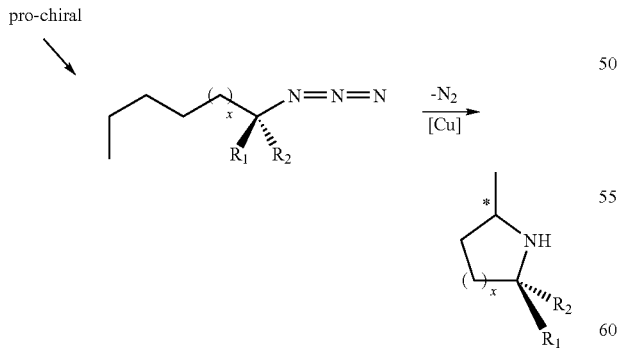

x = 1, 2, 3...
Wherein [Cu] is a copper catalyst system of the present invention, which is chiral.

Catalytic Aziridination of Alkenes with Organoazides

Aspects of the present invention are related to catalytic aziridination of alekenes with organoazides. In certain embodiments, aspects of the present invention are related to aziridine formation with AdN$_3$ under forcing conditions with styrene (Scheme 22). It is not believed that this is a C—H inserted product, as no insertion of NAd into any sp$^2$-hybridized C—H bonds has yet been observed. See also Example 7.

Scheme 22.

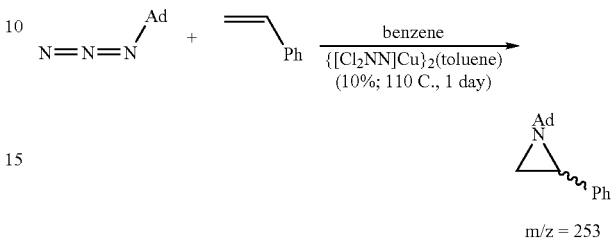

m/z = 253

The ease of aziridination seems to track with the electron-withdrawing properties of the substituent on the nitrene. For instance, aziridination of styrene has been observed (ca. 30%) with the electron-poor azide N$_3$Ar$^F$ (Ar$^F$=3,5-(CF$_3$)$_2$C$_6$H$_3$), though formation of diazene and aniline are competing pathways (Scheme 23). See also Examples 9 and 10.

Scheme 23.

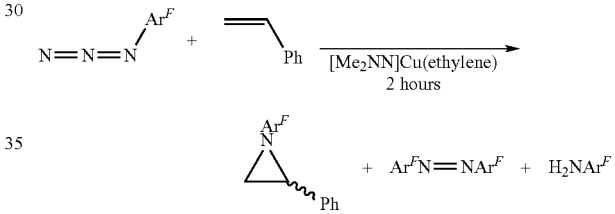

Figure 5:
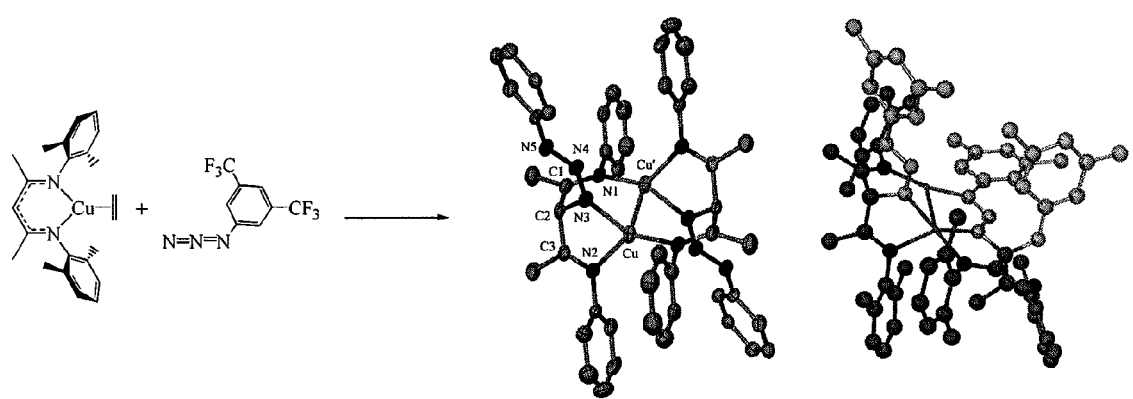
FIG. 5 depicts X-ray structures of catalyst deactivation products with $N_3Ar^F$ show attack of an electrophilic azide (left or right) or nitrene $NAr^F$ fragment (right) on the central C atom of the β-diketiminato backbone.

It has also been determined that attack of the β-diketiminato backbone at the central C atom is a possible pathway for catalyst deactivation. FIG. 5 depicts X-ray structures of catalyst deactivation products with N$_3$Ar$^F$ show attack of an electrophilic azide (left or right) or nitrene NAr$^F$ fragment (right) on the central C atom of the β-diketiminato backbone. Placement of a "protecting group" at this C-atom may be important to achieve higher turnover numbers with a given catalyst, or alternatively it could be sterically protected by using large groups on the two adjacent positions of the backbone, as exemplified in Formulas II and III respectively.

Formula II

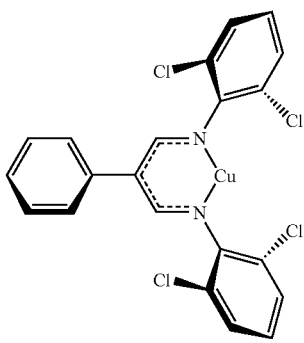

Formula III

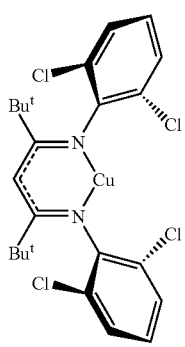

The nitrenes generated from carbonyl azides RC(O)N₃ in the presence of β-diketiminato copper catalysts of the present invention lead to aziridination at room temperature. For instance, PhC(O)N₃ reacts with styrene at room temperature in the presence of 5 mol % {[Cl₂NN]Cu to give the corresponding aziridine (Scheme 24).

Scheme 24.

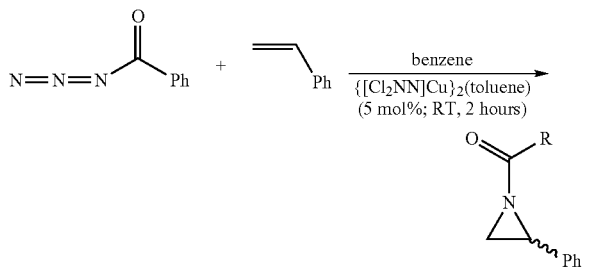

Aspects of the present invention also relates to the use of acyl azides as precursors for hydrocarbon amidation (Scheme 25).

Scheme 25.

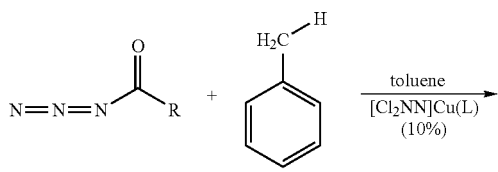

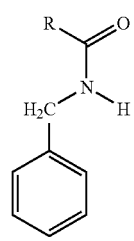

This methodology may be extended to contemplate intramolecular cyclization for lactam synthesis (Scheme 26).

Scheme 26.

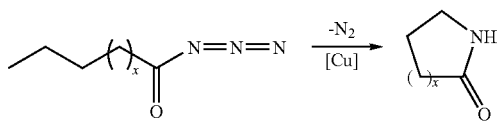

x = 1, 2, 3...
Wherein [Cu] is a copper catalyst system of the present invention.

In certain embodiments, such a transformation could also be chiral (Scheme 27).

Scheme 27.

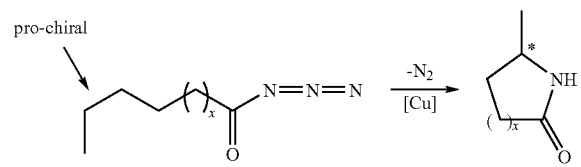

x = 1, 2, 3...
Wherein [Cu] is a copper catalyst system of the present invention, which is chiral.

Catalytic Aerobic Amination of C—H Bonds and Aziridination of Alkenes with Amines Aspects of the present invention relate to catalytic aerobic amination of C—H Bonds and aziridination of alkenes with amines.

The most attractive means of generating a metal-nitrene species [M]=NR capable of doing C—H insertion chemistry or olefin aziridination is by the aerobic oxidation of amines. This is a viable reaction, as copper(I) halides in pyridine in the presence of air will oxidize anilines ArNH₂ to the corresponding azobenzenes ArN=NAr, a reaction which likely proceeds via the intermediacy of some sort of nitrene species (Scheme 28).

Scheme 28.

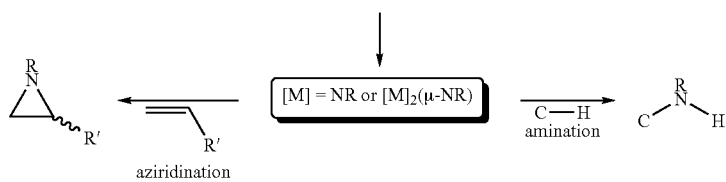

Figure 6:
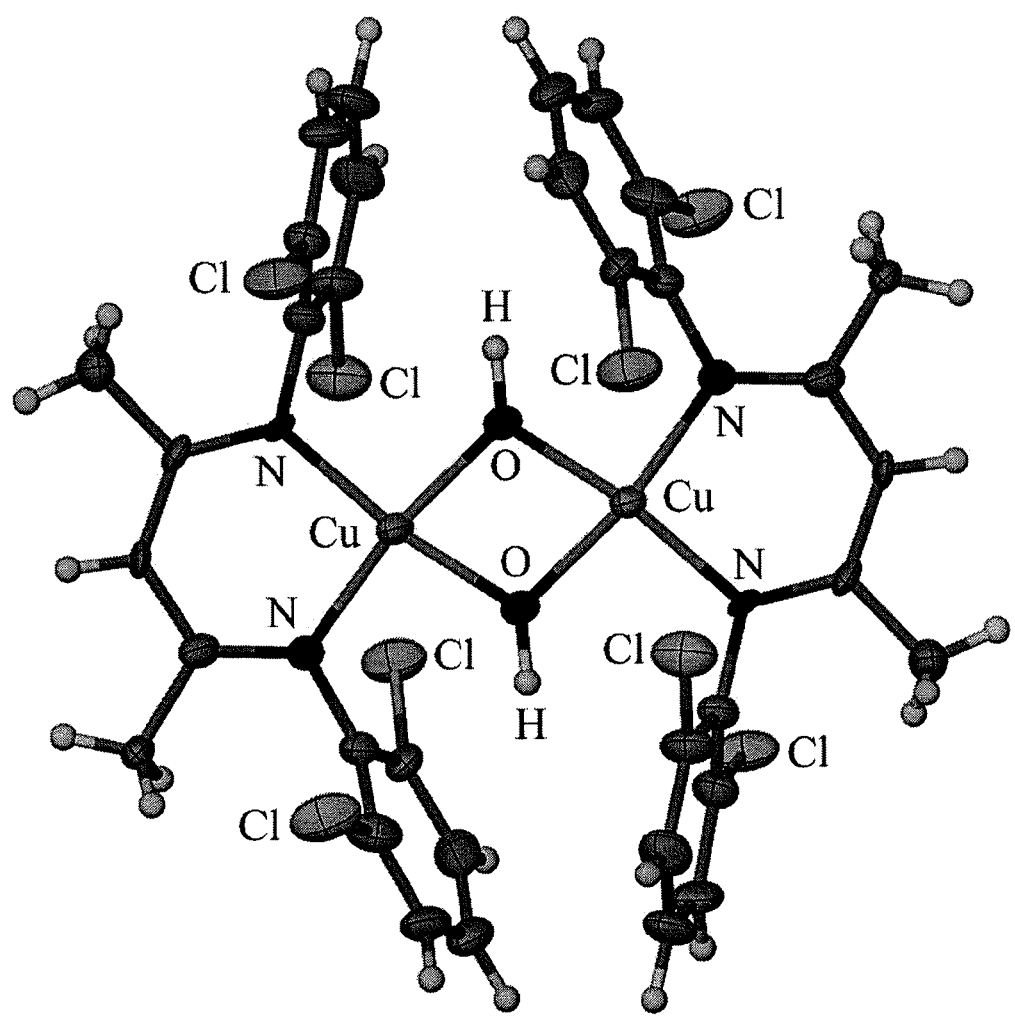
FIG. 6 depicts the X-ray structure of $\{[Cl_2NN]Cu\}_2(\mu\text{-OH})_2$.

The Cu(I) β-diketiminate complexes of the present invention will react with O₂ to give bis(μ-oxo) species [Cu]₂(μ-O)₂ detectable at low temperature. See Aboelella et al. (2002) *JACS*, 124:10660-10661; Spencer et al. (2002) *JACS*, 124: 2108-2109; Spencer et al. (2002) *Inorganic Chemistry*, 41:6307-6321. These reactive bis(μ-oxo) species subsequently react with some sacrificial H-atom donor to give the isolable bis(μ-hydroxy) complexes [Cu]₂(μ-OH)₂ (Scheme 29). See Dai, X. and Warren, T. H. (2001) *Chem. Commun.*, 1998-1999. FIG. 6 depicts the X-ray structure of {[Cl₂NN]Cu}₂(μ-OH)₂.

Scheme 29.

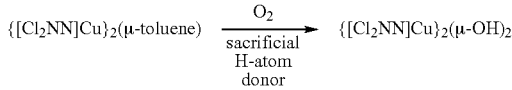

Figure 7:
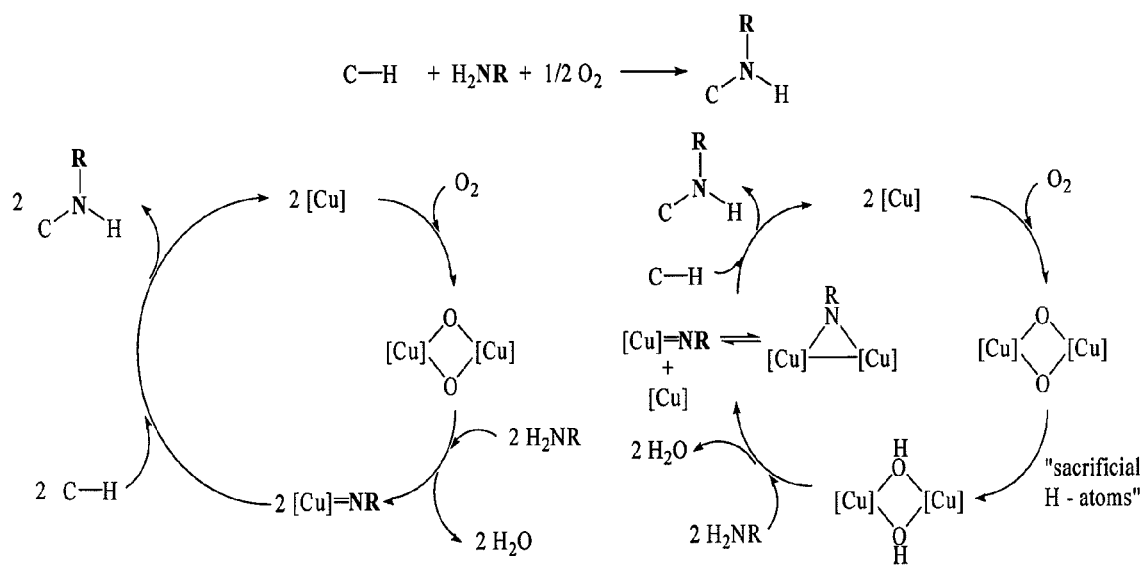
FIG. 7 depicts possible catalytic cycles for aerobic C—H amination reactions.

In certain embodiments of the present invention, an amine H₂NR can be used in the presence of oxygen and the β-diketiminato copper catalyst {[Cl₂NN]Cu}₂(μ-toluene) to form a product in which new N—C bonds are formed. For example, the imine PhCH=NAd is formed in ca. 10-20% yield after heating in air at 110° C. for 1 day (Scheme 30). FIG. 7 depicts possible catalytic cycles for aerobic C—H amination reactions.

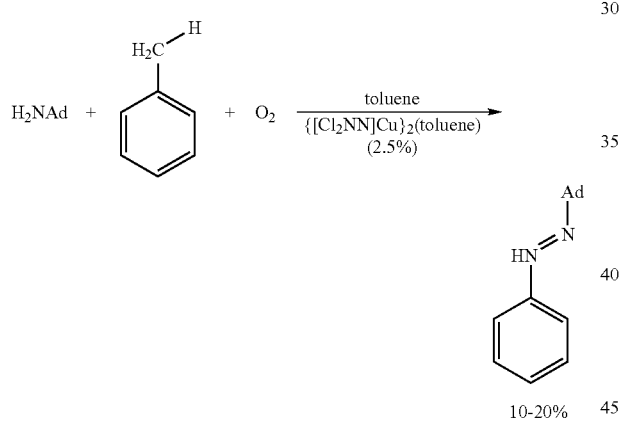

As the pKa of primary organic amides is ca. 17, while that for primary amines is 33-37, it is suspected that this reaction will be favored for amines H₂NR which are more acidic, such as organic amides H₂NC(O)R (pKa ca. 17) versus primary amines H₂NBu$^t$ (pKa ca. 37). This should make reactions such as those represented in Schemes 26 and 27 far more favorable. Such reactions open all of the organoazide reactivity to organic amides and oxygen, significantly enriching the value of the reaction.

Scheme 31.

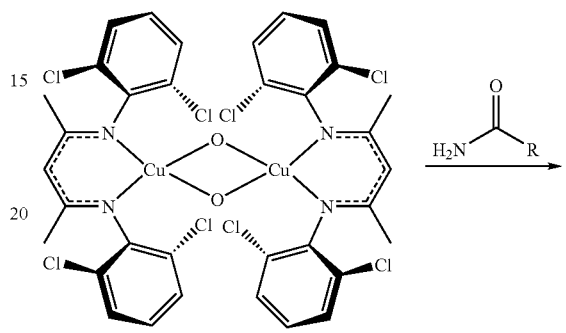

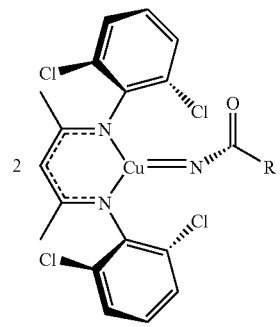

Scheme 32.

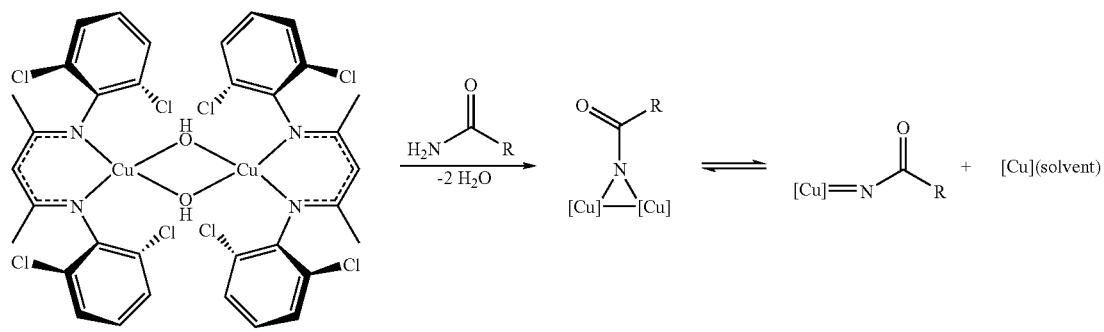

Aspects of the present invention contemplate the use of organic amides as precursors for hydrocarbon amidation (Scheme 33).

Scheme 33.

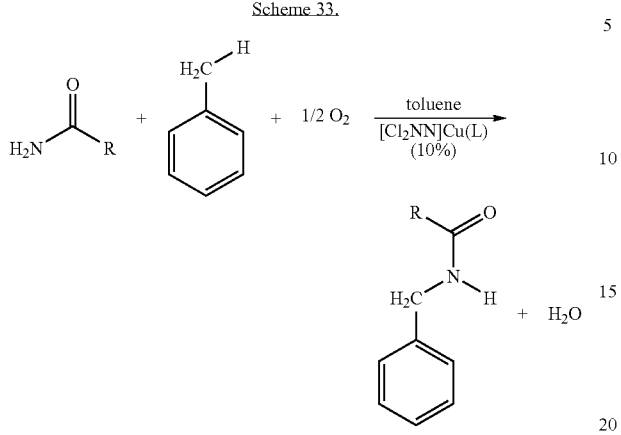

Similarly, such aerobic protocols that can generate metal nitrene species [Cu]=NR should be amenable to catalytic aerobic aziridination of alkenes with amines (Scheme 34).

Scheme 34.

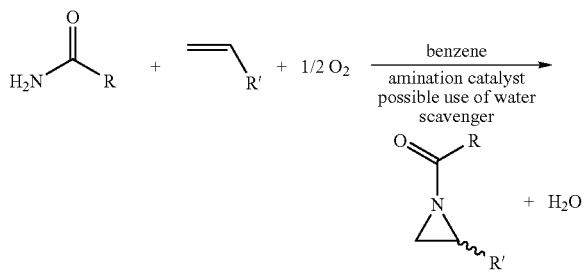

This methodology may be extended to contemplate intramolecular cyclization for lactam synthesis (Scheme 35).

Scheme 35.

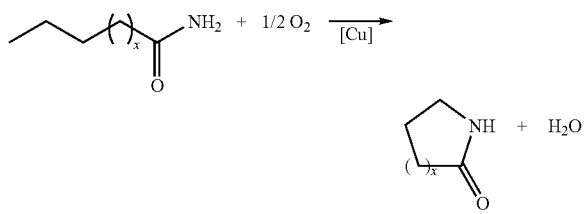

x = 1, 2, 3...
Wherein [Cu] is a copper catalyst system of the present invention.

In certain embodiments, such a transformation could also be chiral (Scheme 36).

Scheme 36.

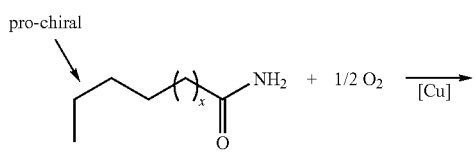

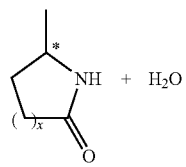

x = 1, 2, 3...
Wherein [Cu] is a copper catalyst system of the present invention, which is chiral.

In certain embodiments, this allows "photochemical" type reactivity under thermal conditions, and under some conditions, at modest temperatures.

Scheme 37.

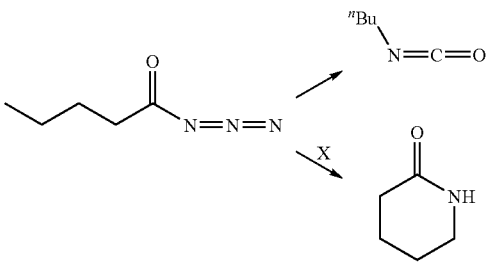

Thermal reactivity of acyl azides favors Curtius rearrangement

We have also found that $\{[Cl_2NN]Cu\}_2$(benzene) reacts cleanly in benzene with excess dioxygen to give $\{[Cl_2NN]Cu\}_2(\mu\text{-O})_2$ (UV-vis; $\lambda$=344 and 396 nm). These UV-vis signatures are similar to those of other established β-diketiminato $[Cu]_2(\mu\text{-O})_2$ complexes (Tolman et al. *JACS*, 2002, 124, 2108; *Inorg. Chem.* 2002, 41, 6307.)

The green $\{[Cl_2NN]Cu\}_2(\mu\text{-O})_2$ can be isolated and reacts with aryl amines to give blue solutions with concomitant formation of azobenzenes and N,N'-diarylhydrazines. When performed in the presence of secondary benzylic amines with bulky anilines such as 2,6-diisopropylaniline, the C—H insertion product (secondary amine) can also be observed by GC/MS.

If the reaction of the $[Cu]_2(m\text{-OH})_2$ species affords entry into a productive catalytic cycle, it would offer the opportunity to use these air-stable species for aerobic amination of C—H bonds with amines. One advantage of the copper systems of the present invention is that the copper nitrene intermediates are thought to be singlet species—the favorable species for C—H insertion chemistry.

Figure 8:
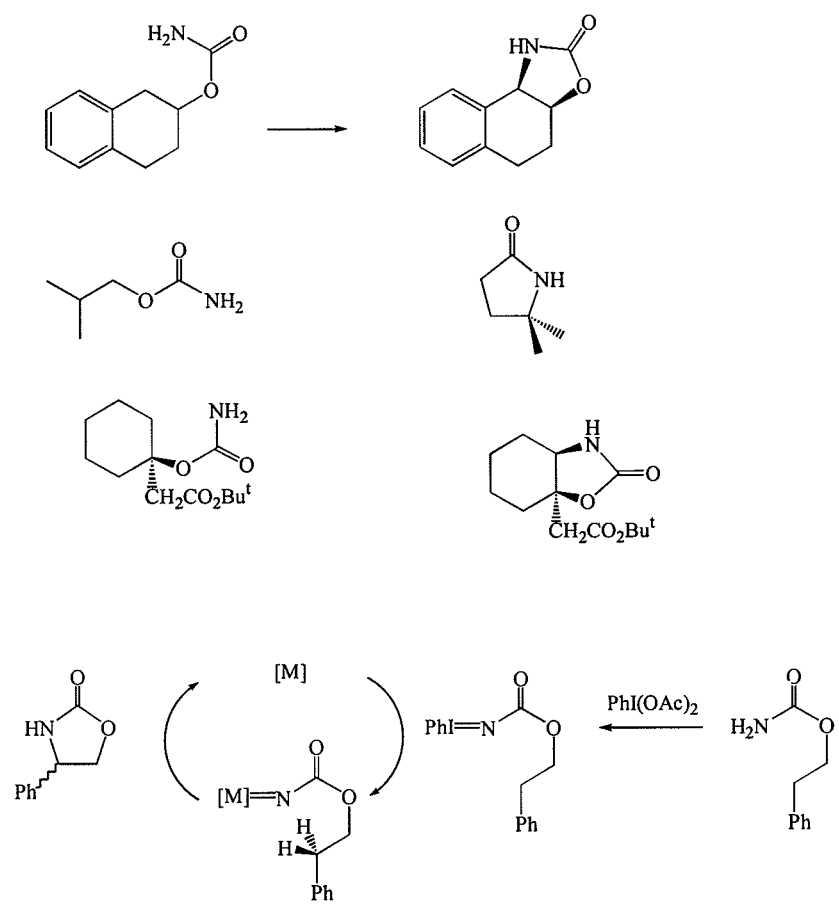
FIG. 8 depicts examples of intermolecular and intramolecular C—H insertion chemistry.

Electron-poor amines have been used by DuBois in conjuction with powerful, but environmentally unfriendly oxidants such as $PhI(OAc)_2$ to effect intramolecular and intermolecular C—H insertion chemistry of a formal carbonyl nitrene (see FIG. 8). The state of the art for intermolecular reactions utilizes either PhI=NTs or a combination of a very electron-poor amine/amide with $PhI(OAc)_2$ to generate an intermediate PhI=NR(R=Ts, Ns, $SO_2Me$, $COCF_3$).

Aspects of the present invention also contemplate the use of different catalysts for the reactions in certain embodiments, including but not limited to the following examples: Ru(II) or Mn(II) porphyrins, which may be chiral; $Rh_2$ dimers; Co(II)-porphyrins with $ArN_3$ (e.g., for intermolecular); copper tris(pyrazolyl)borates (e.g., intermolecular with PhI=NTs or NaNTsCl).

Aspects of the present invention contemplate variations on the types of intermolecular reactions for which embodiments of the present invention may be applicable, including but not limited to the following examples: generally activated bonds;

benzyl; allylic; secondary; those utilizing PhI=NTs or NaNTsCl, H$_2$NSO$_3$CH$_2$CCl$_3$+PhI(OAc)$_2$, MeCH$_2$Ph-OMe, and/or cyclooctane.

Aspects of the present invention contemplate variations on the types of intramolecular reactions for which embodiments of the present invention may be applicable, including but not limited to the following examples: PhI=NSO$_2$CH$_2$CH$_2$R—intramolecular cyclization; ROCONH$_2$+PhI(OAc)$_2$ to generate PhI=NCOOR intermediate; H$_2$CON(SO$_3$R)CH$_2$CH$_2$R—urea-type; H$_2$SO$_2$N(Boc)CH$_2$R sulfamide substrates.

Aspects of the present invention contemplate alleviating some of the associated challenges such as the fact that aliphatic nitrenes normally rearrange and do not work with catalysts; that aryl nitrenes demonstrate only some cases of insertion, with poor yield and selectivity; that amides NC(O)XR require the use of very electron-poor species; and/or that the use of PhI(OAc)$_2$ as an oxidant is too expensive for very large scale use.

As detailed herein, aspects of the present invention relate to many opportunities and certain embodiments of the present invention provide many advantages. Key finding here is that o-substituents on N-aryl ring should not contain H atoms, rendering it prone to interact with the metal-nitrene functionality. For example, copper nitrenes are generated when copper(I) β-diketiminates are exposed to organoazides. These can suffer from attack of nitrene on sp$^3$-hybridized C—H bonds of N-aryl substituents, which can be blocked by use of halogen containing substituents. In certain embodiments, the catalysts can be made resistant to reaction with active [Cu]+ NR intermediates by (1) removing benzylic C—H bonds (i.e., place halogens around the active intermediate); and/or (2) manipulating the backbone nucleophilicity. In the latter instance, it has been demonstrated that some reactions attack at the critical backbone C-atom, therefore, in certain embodiments, placement of a "protecting group" at this C-atom may be important to achieve higher turnover numbers with a given catalyst, or alternatively it could be sterically protected by using large groups on the two adjacent positions of the backbone.

Singlet nitrenes are known for stereospecific insertion. This allows for stereochemistry presently in molecule to be retained, or for stereoselection to take place by interaction of the substrate with a chiral catalyst. As discussed above, so long as the active intermediate is a singlet nitrene, retention of stereochemistry is to be expected. The data for the copper-nitrene complexes of the present invention demonstrate that the intermediates generated are singlets (i.e., NMR evidence and reactivity data in the alkyl case, and DFT evidence in the acyl case). In this regard, we have been able to demonstrate conclusively that the terminal nitrene [Cu]=NAd is diamagnetic. Both $^1$H NMR spectra (δ 5.003 ppm for backbone C—H peak) as well as an Evans method measurements support the diamagnetic nature of [Cl2NN]Cu=NAd. Thus, the active species is a singlet species, which species are associated with clean, stereospecific insertion. Therefore, the complexes of the present invention are suitable for elaboration for use in chiral chemistry.

Aspects of the present invention relate to the use of amines and O$_2$ as the terminal oxidant. Evidence has been presented herein that nitrene intermediates can be generated with O$_2$, which should be assisted by the use of more NH-acidic amides, thus making it available to do on a large scale and very cheaply. In order to deal with the water that is generated, aspects of the present invention contemplate that the catalyst is stable towards any water formed, for example, by use of a chemical scavenger or manipulation of the ligand to make it less basic.

Additional Transformations

Imines may be formed by subsequent oxidation of a secondary benzyl amine formed via C—H insertion into a primary benzylic. For instance, the use of two equivalents of N$_3$Ad in the amination of toluene gave the benzylic imine NAd=CHPh in 60% yield.

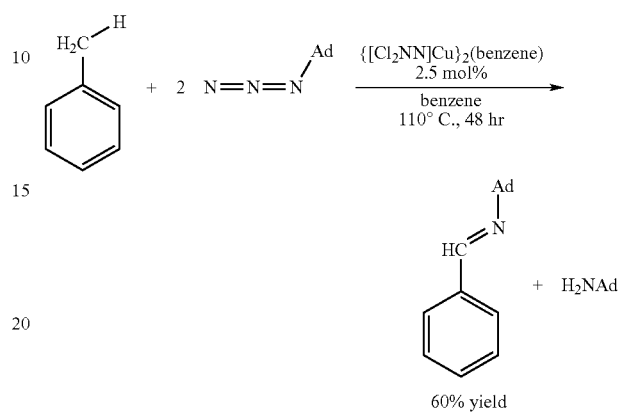

Conceivably, this overall transformation could be catalyzed by exposure of the initial product (using 1 equiv. azide), i.e., a secondary amine, to oxygen in the presence of the catalyst; this embodiment is prophetic.

Imines might also be formed by tandem insertion of a nitrene into C—H bond alpha to an ether, and expulsion of an alcohol. For example, amines alpha to ether functionalities are known to be susceptible to the loss of alcohol to give the corresponding imine. In certain embodiments, the methods of the present invention favor C—H insertion into a C—H bond alpha to an ether moiety. The overall transformation is summarized in the scheme below.

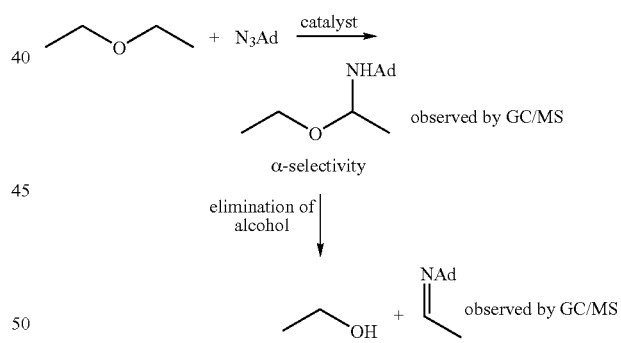

DEFINITIONS

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

For purposes of this invention, the chemical elements are identified in accordance with the Periodic Table of the Elements, CAS version, Handbook of Chemistry and Physics, 67th Ed., 1986-87, inside cover.

A "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "reaction product" means a compound which results from the reaction of the catalyst and the alkene substrate. In general, the term "reaction product" will be used herein to refer to a stable, isolable compound, and not to unstable intermediates or transition states.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

% Enantiomeric Excess $A(ee)$=(% Enantiomer $A$)–(% Enantiomer $B$)

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e., one-half mole of reagent per mole of racemic substrate). Examples of catalytic reactions which have been used for kinetic resolution of racemic reactants include the Sharpless epoxidation and the Noyori hydrogenation.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 of fewer. Likewise, preferred cycloalkyls have from 4-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

The terms "alkenyl" and "alkynyl" refer to unsaturated aliphatic groups analogous in length and possible substitution to the alkyls described above, but which contain at least one double or triple carbon-carbon bond, respectively.

The term "$Me_2NN$" refers to a moiety represented by the general formula:

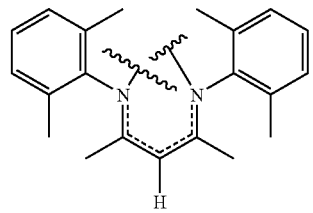

The term "$Cl_2NN$" refers to a moiety represented by the general formula:

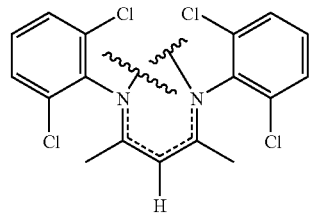

As used herein, the term "amino" means —$NH_2$; the term "nitro" means —$NO_2$; the term "halogen" designates —F, —Cl, —Br or —I; the term "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

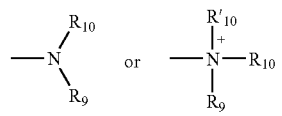

wherein $R_9$, $R_{10}$ and $R'_{10}$ each independently represent a group permitted by the rules of valence.

The term "acylamino" is art-recognized and refers to a moiety that can be represented by the general formula:

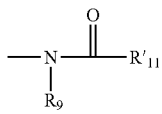

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art-recognized as an amino-substituted carbonyl and includes a moiety that can be represented by the general formula:

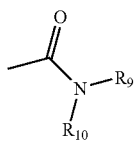

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art-recognized and includes such moieties as can be represented by the general formula:

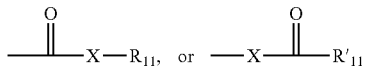

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art-recognized and includes a moiety that can be represented by the general formula:

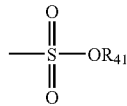

in which $R_{41}$ is an electron pair, hydrogen, alkyl, cycloalkyl, or aryl.

The term "sulfonylamino" is art-recognized and includes a moiety that can be represented by the general formula:

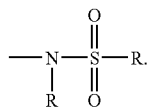

The term "sulfamoyl" is art-recognized and includes a moiety that can be represented by the general formula:

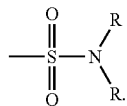

The term "sulfonyl", as used herein, refers to a moiety that can be represented by the general formula:

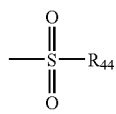

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

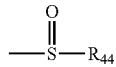

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

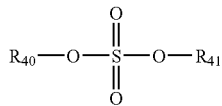

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or —(CH$_2$)$_m$—R$_7$, —CF$_3$, —CN, or the like.

The term "heteroatom" as used herein means an atom of any element other than carbon or hydrogen. Preferred heteroatoms are nitrogen, oxygen, sulfur, phosphorus and selenium.

The terms ortho, meta and para apply to 1,2-, 1,3- and 1,4-disubstituted benzenes, respectively. For example, the names 1,2-dimethylbenzene and ortho-dimethylbenzene are synonymous.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Compounds of the Invention

The following are some important aspects of catalysts contemplated by certain embodiments of the present invention. With reference to the structure of Formula IV, it is important in certain embodiments that the substituents X$_1$-X$_4$ should not contain benzylic C—H bonds; however, aryl C—H bonds are not problematic. See, for example, the results presented in FIG. 10. R$_7$-R$_9$ may have H atoms; sample R$_7$-R$_9$ substituents include, but are not limited to: H, Me, CF$_3$, Ph, and t-Bu. The complex may be manipulated via electronic tuning to make it more or less electron-rich. The complexes of the present invention may also be represented by Formula V, wherein R may be aryl (e.g., a halogenated aryl, such as C$_6$F$_5$), or heteroaryl.

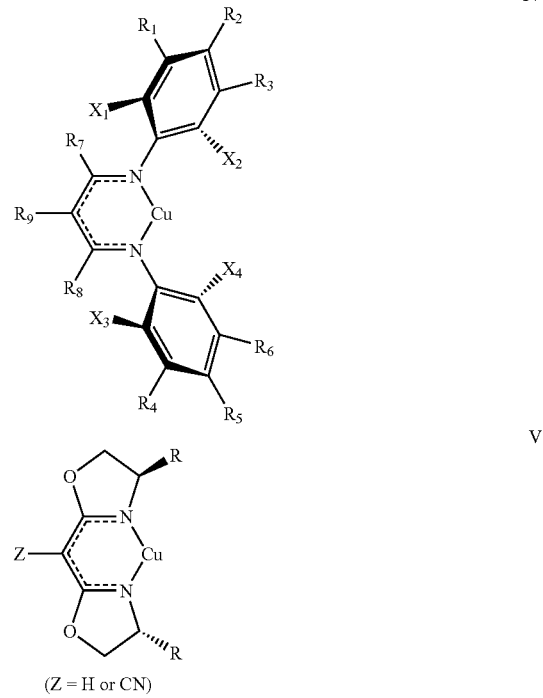

For example, the formation of copper nitrenes using the ligand V above (with R=Ph and Z=H) has been validated. The free bis(oxazoline) was reacted with a stoichiometric amount of CuOBu$^t$ on a ca. 0.1 mmol scale in benzene, and the solution was taken to dryness to remove the HOBu$^t$ formed. The solid was redissolved in benzene and 1 equiv. N$_3$Ad was added, resulting in the formation of a deep violet solution. Monitoring by UV-vis spectroscopy gives a $\lambda_{max}$ near 570 nm, similar to that observed for the terminal copper nitrene [Cl$_2$NN]Cu=NAd ($\lambda_{max}$=583 nm). In contrast, the dicopper nitrene {[Cl$_2$NN]Cu}$_2$(μ-NAd) possesses a $\lambda_{max}$=717 nm.

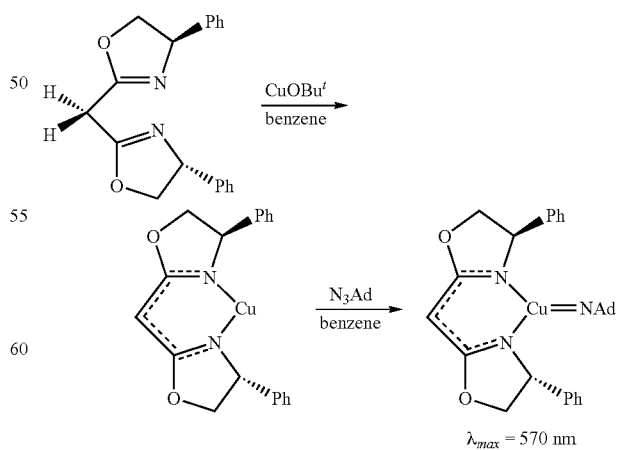

In certain embodiments, the complexes may be used with a chiral Lewis base (L*) (Scheme 38).

Scheme 38.

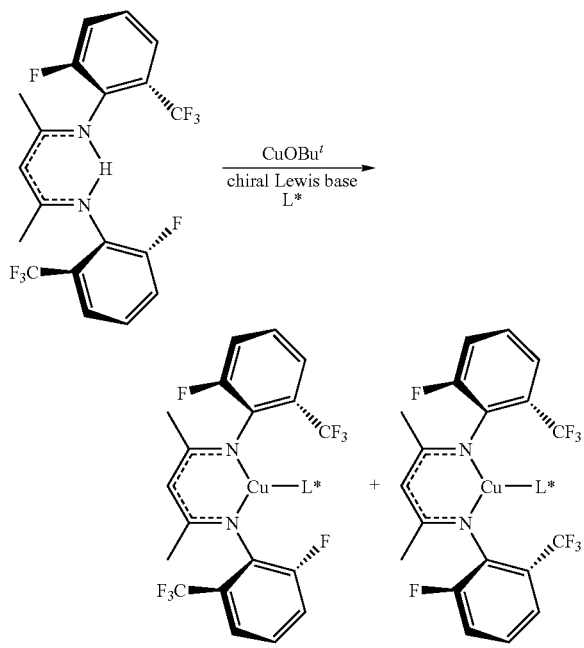

One aspect of the present invention relates to a compound represented by Formula IV:

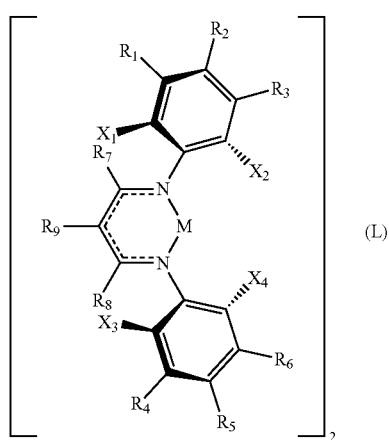

wherein,

R1-R9 represents independently for each occurrence H, alkyl, aryl, aralkyl, halogen, CN, or $CF_3$;

X1-X4 are hydrogens, halogens or perhaloalkyls

L is a Lewis base or O; and

M is Cu or Co.

In certain embodiments, the present invention relates to the aforementioned compound and any attendant definitions, wherein M is Cu.

In certain embodiments, the present invention relates to the aforementioned compound and any attendant definitions, wherein M is Co.

In certain embodiments, the present invention relates to the aforementioned compound and any attendant definitions, wherein R7-R9 represents independently for each occurrence H, Me, $CF_3$, Ph, or t-Bu.

In certain embodiments, the present invention relates to the aforementioned compound and any attendant definitions, wherein R7 and R8 represent t-Bu.

In certain embodiments, the present invention relates to the aforementioned compound and any attendant definitions, wherein X1-X4 are independently for each occurrence halogen or perfluoroalkyl.

In certain embodiments, the present invention relates to the aforementioned compound and any attendant definitions, wherein X1-X4 are independently for each occurrence Cl, I, Br, or $CF_3$.

In certain embodiments, the present invention relates to the aforementioned compound and any attendant definitions, wherein X1-X4 are independently for each occurrence Cl.

In certain embodiments, the present invention relates to the aforementioned compound and any attendant definitions, wherein X1-X4 are independently for each occurrence $CF_3$.

In certain embodiments, the present invention relates to the aforementioned compound and any attendant definitions, wherein M is Cu, and X1-X4 are independently for each occurrence Cl.

In certain embodiments, the present invention relates to the aforementioned compound and any attendant definitions, wherein M is Cu, and X1-X4 are independently for each occurrence $CF_3$.

In certain embodiments, the present invention relates to the aforementioned compound and any attendant definitions, wherein L is aromatic.

In certain embodiments, the present invention relates to the aforementioned compound and any attendant definitions, wherein L is toluene.

In certain embodiments, the present invention relates to the aforementioned compound and any attendant definitions, wherein L is O.

In certain embodiments, the present invention relates to the aforementioned compound and any attendant definitions, wherein M is Cu, X1-X4 are independently for each occurrence Cl, and L is toluene.

In certain embodiments, the present invention relates to the aforementioned compound and any attendant definitions, wherein M is Cu, X1-X4 are independently for each occurrence $CF_3$, and L is toluene.

METHODS OF THE INVENTION

One aspect of the present invention relates to a method of C—H bond amination depicted in Scheme A:

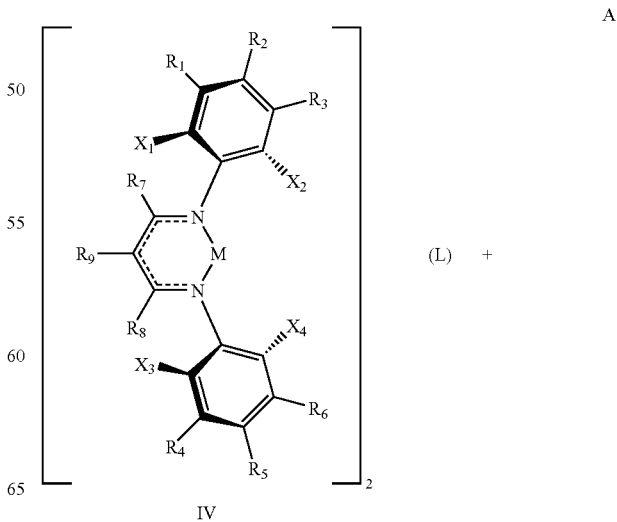

-continued

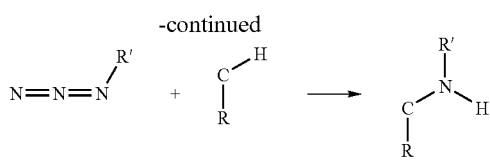

wherein,

R represents alkyl, alkenyl, alkynyl, aralkyl, aryl or heteroaryl;

R' represents alkyl, alkenyl, alkynyl, aralkyl, aryl or heteroaryl;

R1-R9 represents independently for each occurrence H, alkyl, aryl, aralkyl, halogen, CN, or $CF_3$;

X1-X4 represents independently for each occurrence hydrogen, halogen or perhaloalkyl;

L is a Lewis base or O; and

M is Cu or Co.

In certain embodiments, the present invention relates to the aforementioned method and any attendant definitions, wherein the reaction is catalytic in the compound represented by Formula IV.

In certain embodiments, the present invention relates to the aforementioned method and any attendant definitions, wherein the reaction further comprises the use of oxygen as a reagent.

Another aspect of the present invention relates to a method of C—H bond amidation depicted in Scheme B:

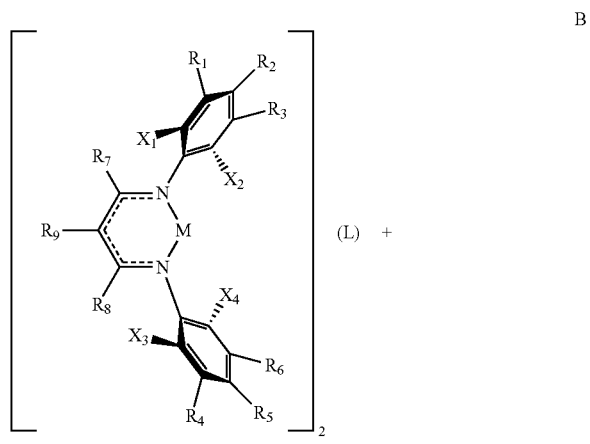

B

IV wherein,

R represents alkyl, alkenyl, alkynyl, aralkyl, aryl or heteroaryl;

R' represents alkyl, alkenyl, alkynyl, aralkyl, aryl or heteroaryl;

R1-R9 represents independently for each occurrence H, alkyl, aryl, aralkyl, halogen, CN, or $CF_3$;

X1-X4 represents independently for each occurrence hydrogen, halogen or perhaloalkyl;

L is a Lewis base or O; and

M is Cu or Co.

In certain embodiments, the present invention relates to the aforementioned method and any attendant definitions, wherein the reaction is catalytic in the compound represented by Formula IV.

In certain embodiments, the present invention relates to the aforementioned method and any attendant definitions, wherein the reaction further comprises the use of oxygen as a reagent.

Another aspect of the invention relates to a method of olefin aziridination depicted in Scheme C:

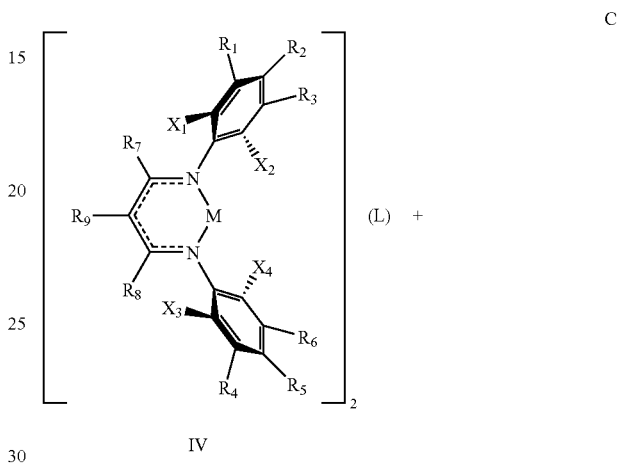

C

IV wherein,

R represents alkyl, alkenyl, alkynyl, aralkyl, aryl or heteroaryl;

R' represents alkyl, alkenyl, alkynyl, aralkyl, aryl or heteroaryl;

R1-R9 represents independently for each occurrence H, alkyl, aryl, aralkyl, halogen, CN, or $CF_3$;

X1-X4 represents independently for each occurrence hydrogen, halogen or perhaloalkyl;

L is a Lewis base or O; and

M is Cu or Co.

In certain embodiments, the present invention relates to the aforementioned method and any attendant definitions, wherein the reaction is catalytic in the compound represented by Formula IV.

In certain embodiments, the present invention relates to the aforementioned method and any attendant definitions, wherein the reaction further comprises the use of oxygen as a reagent.

Another aspect of the invention relates to a method of C—H bond amidation depicted in Scheme D:

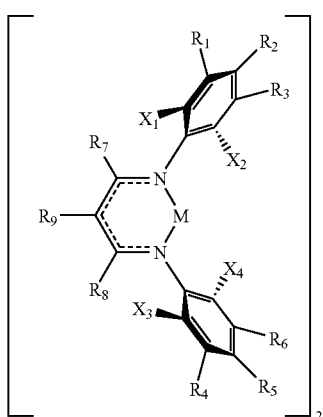

IV

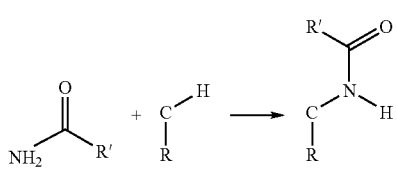

wherein,

R represents alkyl, alkenyl, alkynyl, aralkyl, aryl or heteroaryl;

R' represents alkyl, alkenyl, alkynyl, aralkyl, aryl or heteroaryl;

R1-R9 represents independently for each occurrence H, alkyl, aryl, aralkyl, halogen, CN, or $CF_3$;

X1-X4 represents independently for each occurrence hydrogen, halogen or perhaloalkyl;

L is a Lewis base or O; and

M is Cu or Co.

In certain embodiments, the present invention relates to the aforementioned method and any attendant definitions, wherein the reaction is catalytic in the compound represented by Formula IV.

In certain embodiments, the present invention relates to the aforementioned method and any attendant definitions, wherein the reaction further comprises the use of oxygen as a reagent.

In certain embodiments, the present invention relates to any of the aforementioned methods, wherein M is Cu.

In certain embodiments, the present invention relates to any of the aforementioned methods, wherein M is Co.

In certain embodiments, the present invention relates to any of the aforementioned methods, wherein R7-R9 represents independently for each occurrence H, Me, $CF_3$, Ph, or t-Bu.

In certain embodiments, the present invention relates to any of the aforementioned methods, wherein R7 and R8 represent t-Bu.

In certain embodiments, the present invention relates to any of the aforementioned methods, wherein X1-X4 are independently for each occurrence halogen or perfluoroalkyl. In certain embodiments, the present invention relates to any of the aforementioned methods, wherein X1-X4 are independently for each occurrence Cl, I, Br, or $CF_3$.

In certain embodiments, the present invention relates to any of the aforementioned methods, wherein X1-X4 are independently for each occurrence Cl.

In certain embodiments, the present invention relates to any of the aforementioned methods, wherein X1-X4 are independently for each occurrence $CF_3$.

In certain embodiments, the present invention relates to any of the aforementioned methods, wherein M is Cu, and X1-X4 are independently for each occurrence Cl.

In certain embodiments, the present invention relates to any of the aforementioned methods, wherein M is Cu, and X1-X4 are independently for each occurrence $CF_3$.

In certain embodiments, the present invention relates to any of the aforementioned methods, wherein L is O.

In certain embodiments, the present invention relates to any of the aforementioned methods, wherein L is aromatic.

In certain embodiments, the present invention relates to any of the aforementioned methods, wherein L is toluene.

In certain embodiments, the present invention relates to any of the aforementioned methods, wherein M is Cu, X1-X4 are independently for each occurrence Cl, and L is toluene.

In certain embodiments, the present invention relates to any of the aforementioned methods, X1-X4 are independently for each occurrence $CF_3$, and L is toluene.

In certain embodiments, the present invention relates to any of the aforementioned methods, wherein the compound represented by Formula IV selected from the group consisting of:

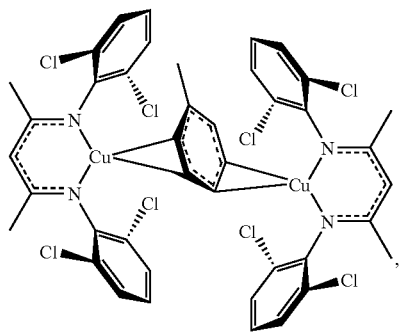

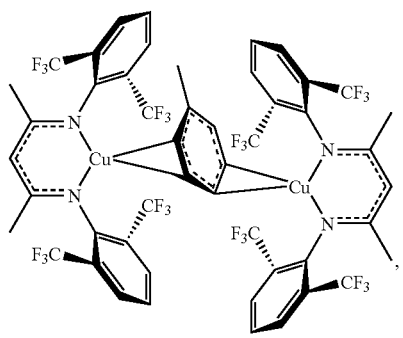

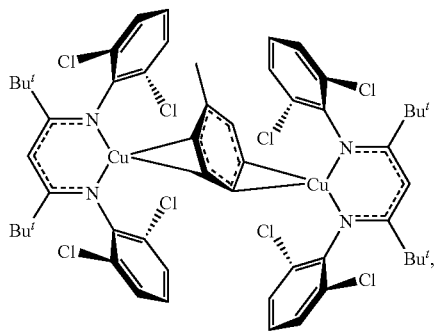

-continued

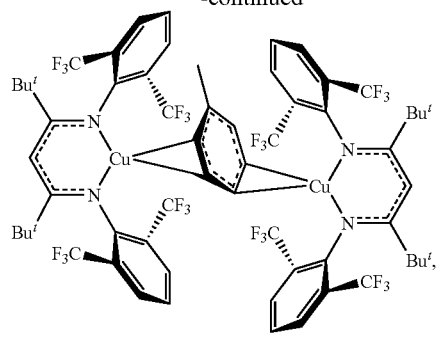

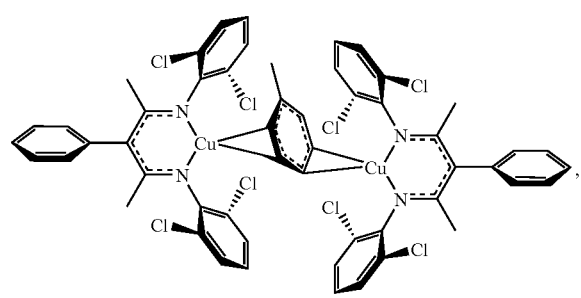

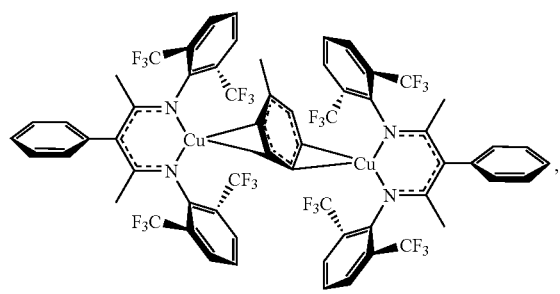

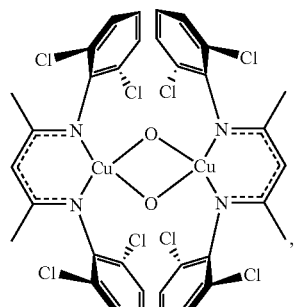

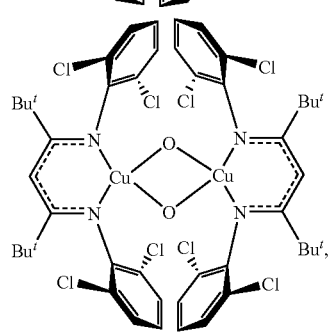

-continued

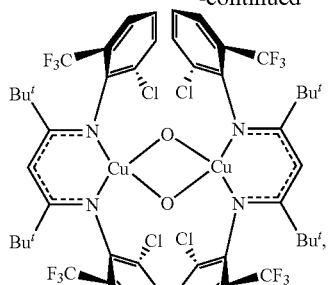

, and

EXEMPLIFICATION

The invention now being generally described, it will be more readily understood by reference to the following examples, which are included merely for purposes of illustration of certain aspects and embodiments of the present invention, and are not intended to limit the invention.

General Experimental Details

All experiments were carried out in a dry nitrogen atmosphere using glovebox and standard Schlenk line techniques when required. 4 Å molecular sieves were activated at 180° C. in vacuo for 24 h. Anhydrous toluene and 1,4-dioxane were purchased from Aldrich and stored over 4 Å molecular sieves prior to use. Diethyl ether ($Et_2O$), tetrahydrofuran (THF), hexane, and pentane were distilled before use from sodium/benzophenone. All deuterated solvents were sparged with nitrogen, dried with 4 Å molecular sieves and stored under nitrogen. $^1H$ and $^{13}C$ spectra were recorded on a Mercury Varian 300 NMR spectrometer at 300 and 75.4 MHz, respectively. All NMR spectra were taken at 25° C. unless otherwise noted and were indirectly referenced to TMS using residual solvent signals as internal standards. GC-MS spectra were recorded on a Fisions Instruments MD800. Infrared spectra were recorded on a Perkin-Elmer Spectrum One FTIR spectrometer using an attenuated internal reflectance sample holder. Elemental analyses were performed on a Perkin-Elmer PE2400 microanalyzer in our laboratories.

Anhydrous 1-adamantylazide was obtained from Strem and used as received. $O_2$ gas (99.5%) was obtained from MG Industries and passed through a drying tube containing $CaCl_2$ prior to use.

X-ray structure refinement details: Single crystals of each compound were mounted under mineral oil on glass fibers and immediately placed in a cold nitrogen stream at $-90(2)°$ C. on a Bruker SMART CCD system. Full spheres of data were collected were collected (0.3° ω-scans; $2θ_{max}=56°$; monochromatic Mo Ka radiation, λ=0.7107 Å) and integrated with the Bruker SAINT program. Structure solutions were performed using the SHELXTL/PC suite and XSEED. See SHELXTL-PC, Vers. 5.10; 1998, Bruker-Analytical X-ray Services, Madison, Wis.; G. M. Sheldrick, SHELX-97, Universität Göttingen, Göttingen, Germany and L. Barbour, XSEED, 1999. Intensities were corrected for Lorentz and polarization effects and an empirical absorption correction was applied using Blessing's method as incorporated into the program SADABS. See SADABS; G. M. Sheldrick, 1996, based on the method described in R. H. Blessing (1995) *Acta Crystallogr., Sect. A,* 51:33. Non-hydrogen atoms were refined with aniostropic thermal parameters and hydrogen atoms were included in idealized positions.

Calibration procedure for quantitative GC/MS analysis: A mixture of styrene (0.253 g, 2.43 mmol), $\{[Me_2NN]Cu\}_2(μ\text{-}CPh_2)$ (0.110 g, 0.122 mmol) and 5 mL of toluene was stirred until the solution turned to light yellow, and then naphthalene (0.028 g) was added as standard. Since analysis by GC/MS showed that the only other $CPh_2$-containing species $Ph_2C=CPh_2$ was present in an extremely low amount (<1%), the carbene group ($CPh_2$) was essentially quantitatively (>99%) transferred to styrene to form a cyclopropane; thus we assume that the mass of the yet formed cyclopropanation is the theoretical yield based on the starting material of $\{[Me_2NN]Cu\}_2(μ\text{-}CPh_2)$ that allows the following equation to be developed:

$$\frac{M(\text{mass of cyclopropanation})}{M(\text{mass of naphthalene})} = \frac{S\begin{pmatrix}\text{peak area of} \\ \text{cyclopropanation}\end{pmatrix}}{S\begin{pmatrix}\text{peak area of} \\ \text{naphthalene}\end{pmatrix}} * R(\text{factor})$$

Then this R(factor) can be applied to other cyclopropanation yield calculations by adding a certain amount of naphthalene as a internal standard.

Example 1

Synthesis of $\{[Cl_2NN]Cu\}_2$(toluene) 7

A chilled solution at $-35°$ C. of potassium tert-butoxide (1.95 g, 0.017 mmol) in 10 mL THF was added to a suspension of copper(I) iodide (3.00 g, 0.015 mmol) in 20 mL of THF. The mixture was stirred overnight at room temperature. The THF was removed in vacuo and the solid residue was dissolved in toluene, filtered on Celite and the volatiles were then removed in vacuo. A pale yellow solid was obtained and washed with 5 mL of cold pentane to afford 0.280 g (83%) of pure copper(I) tert-butoxide. To a solution of copper(I) tert-butoxide (0.630 g, 4.617 mmol) in 10 mL toluene, a solution of $H[Cl_2NN]$ (1.40 g, 3.846 mmol) in 5 mL of toluene was added and stirred for 2 hrs. The volatiles were removed in vacuo, and the yellow residue obtained was washed with 5 mL of pentane to afford 1.8 g (94%) of 7 as a pale yellow powder. The powder was dissolved in toluene and the solution was filtered through Celite and the volatiles were removed in vacuo. The resulting solid was further recrystallized with 1:3 mixture of toluene/pentane at $-35°$ C. to afford colorless crystals that were suitable for X-ray diffraction. $^1$H NMR (300 MHz, benzene-$d_6$): 7.116-7.067 (m, 8, Ar-o-H), 6.450 (t, 4, Ar-p-H), 4.830 (s, 2, backbone-CH), 2.106 (s, 3, toluene-$CH_3$), 1.705 (s, 12, backbone-$CH_3$).

Example 2

Synthesis of $\{[Cl_2NN]Cu\}_2$(m-NAd)

1-Adamantylazide (0.030 g, 0.172 mmol) was dissolved in 3 mL ether and added to a stirring solution of $\{[Cl_2NN]Cu\}_2$(toluene) 7 (0.170 g, 0.172 mmol) in 5 mL ether at room temperature. The solution turned green after 5 min and bubbling of $N_2$ gas was observed. The solution was stirred for 30 minutes, filtered through Celite and the filtrate was concentrated in vacuo to ca. 3 mL. The solution crystallized overnight at $-35°$ C. to afford 0.100 g (56%) of dark green powder and upon recrystallization with 1:1 mixture of ether/pentane, crystals suitable for X-ray diffraction were obtained. $^1$H NMR (300 MHz, benzene-$d_6$): δ 7.018-6.990 (br m, 8, 7.018-6.990), 6.395 (t, 4, Ar-p-H), 5.144 (s, 2, backbone-CH), 1.639 (s, 12, backbone-$CH_3$), 1.311-1.200 (br, m, Ad-H).

Example 3

Synthesis of $\{[Me_3NN]Cu\}_2$(m-NAd)

1-Adamantylazide (0.056 g, 0.316 mmol) was dissolved in 5 mL ether and added to a stirring solution of $\{[Me_3NN]Cu\}_2$(toluene) (0.255 g, 0.288 mmol) in 5 mL ether at room temperature. The solution turned green after 5 min and bubbling of $N_2$ gas was observed. The solution was stirred for 30 minutes, filtered through Celite and the filtrate was concentrated in vacuo to ca. 3 mL. The solution crystallized overnight at $-35°$ C. to afford 0.130 mg (47%) of dark green crystals and upon recrystallization from pentane, crystals suitable for X-ray diffraction were obtained. $^1$H NMR (300 MHz, benzene-$d_6$): δ 6.920-6.701 (br m, 8, Ar—H), 5.028 (s, 2, backbone-CH), the $^1$H NMR is very complex in the aliphatic region.

Example 4

Synthesis of $[AdCH_2NN_B]CuNAd$

To a solution of $[Me_2NN_B]Cu(H_2C=CHC(CH_3)_3)$ (0.175 g, 0.330) in 5 mL of toluene a solution of 1-Adamantylazide (0.116 g, 0.650 mmol) was added in 5 mL of toluene. The color of the solution changes instantly from a yellow to a deep orange red color. The solution was stirred for 1 hr, filtered through Celite, and the volatiles were removed in vacuo. The residue was extracted in 5 mL ether, filtered through Celite and concentrated to ca. 2 mL and allowed to stand at $-35°$ C. overnight. Orange-red crystals were collected from the solution to afford 0.70 g (48%) of the product that were suitable for X-ray diffraction. $^1$H NMR (300 MHz, benzene-$d_6$): δ 6.970-6.860 (br m, 6, Ar—H), 5.302 (br, 1, backbone-CH), the remaining $^1$H NMR chemical shifts are very broad and very complex to interpret.

Example 5

Catalytic Amination Reactions with $N_3Ad$

To a solution of 7 (0.025 mmol) dissolved in neat solvent 10 mL, 1-Adamantylazide (1 mmol) was added in 10 mL of solvent. A dark greenish solution is observed at room temperature and the formation of the nitrene inserted product is observed by $^1$H NMR and GC/MS at different reactions times and temperatures as reported below (Table 1).

TABLE 1

Catalytic amination with of C—H bonds from 1-Adamantylazide.

| Entry | Substrate | Product | Time | Yield |
|---|---|---|---|---|
| 1 | (toluene) | PhCH$_2$NHAd | 3 hr | >95%[a] |
| 2 | (cyclohexane) | Cy-NHAd | 1.5 hr | 90%[b] |
| 3 | (dioxane) | dioxanyl=NAd | 3 hr | Quantitative[c] |

[a]Reaction done thermally T = 110° C. with 2.5 mol % of 7 as determined by $^1$H NMR.
[b]Reaction carried out by microwave assisted radiation T = 120° C. with 2.5 mol % of 7, yield determined by isolation method.
[c]Reaction done with Microwave, T = 110° C., product observed by GC/MS analysis, m/z = 235.

Example 6

Generation of a Terminal Nitrene [Cl$_2$NN]Cu=NAd Species

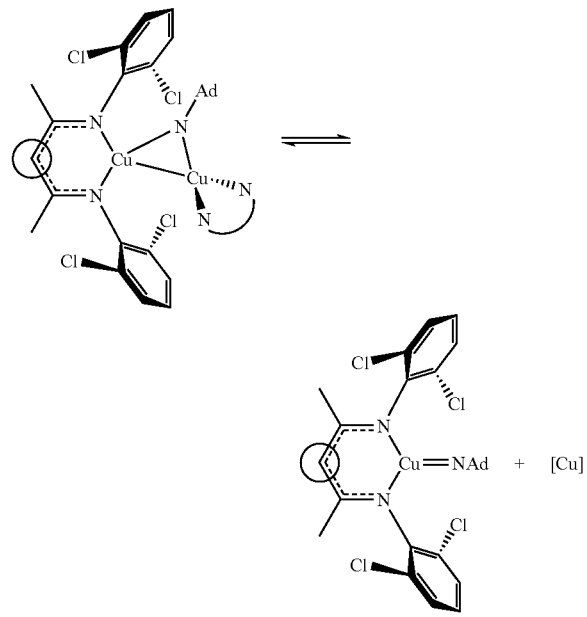

1-Adamantylazide (0135 g, 0.755 mmol) was dissolved in 5 mL cyclohexane and added to a stirring solution of {[Cl$_2$NN]Cu}$_2$(toluene) 7 (0.300 g, 0.330 mmol) in 5 mL cyclohexane at room temperature. The solution turned green after 5 min and bubbling of N$_2$ gas was observed. The solution was stirred for two days at 100° C. A blue solution was obtained which was filtered through Celite and the volatiles were removed in vacuo. $^1$H NMR of the crude solution shows the formation of a terminal species (Table 2 and FIG. 4). $^1$H NMR (300 MHz, benzene-d$_6$): δ 7.018-6.990 (m, 4, Ar-o-H), 6.385 (t, 2, Ar-p-H), 5.003 (s, 1, backbone-CH), 1.393 (s, 6, backbone-CH$_3$).

TABLE 2

$^1$H NMR chemical shifts in benzene-d$_6$ for dicopper nitrene complex, terminal nitrene complex, and the dicopper toluene complex.

| Complex | δ backbone C—H (ppm) |
|---|---|
| {[Cl$_2$NN]Cu}$_2$(µ-NAd) | 5.142 s |
| [Cl$_2$NN]Cu=NAd | 5.003 s |
| {[Cl$_2$NN]Cu}(toluene) | 4.829 br |

Example 7

Catalytic Aziridination Reactions with N$_3$Ad

To a solution of {[Cl$_2$NN]Cu}$_2$(µ-toluene) 7 (0.05 mmol) dissolved in benzene (10 mL), a solution of 1-adamantylazide (1 mmol) in 5 mL of benzene was added followed by the subsequent addition a solution of styrene (1 mmol) in 2 mL of benzene. The solution turns dark green in 10 min at room temperature and the reaction was then heated at 90° C. overnight. GC/MS analysis of the reaction mixture shows the formation of the corresponding aziridine with m/z=253, in addition to some unreacted azide. Aziridine yield ca. 20%.

Example 8

Catalytic Aziridination Reactions with PhCON

To a solution of {[Cl$_2$NN]Cu}$_2$(µ-toluene) (0.05 mmol) dissolved in benzene 10 mL, a solution of the benzoyl azide (1 mmol) in 5 mL of benzene was added followed by the subsequent addition a solution of styrene (1 mmol) in 2 mL of benzene. The solution turns dark instantaneously and the reaction was stirred at room temperature for 3 hrs. GC/MS analysis indicated the formation of the corresponding aziridine with m/z=223, in addition to some unreacted azide. Aziridine yield ca. 30%.

Example 9

Cu(I) Catalyzed Aziridination of Styrene and N$_3$Ar$^F$

A solution of N$_3$Ar$^F$ (0.149 g, 0.76 mmol) in 5 mL CH$_2$Cl$_2$ was added dropwise to a solution of [Me$_2$NN]Cu(styrene) (0.018 g, 0.038 mmol) and styrene (0.158 g, 1.52 mmol) in 5 mL CH$_2$Cl$_2$. The mixture was stirred for another hour and a ca. 20% of aziridine was identified by GC-MS analysis.

About a 50% yield of aziridine was obtained using [Me$_2$NN$_B$]Cu(ethylene) as a catalyst following the same procedure described above.

Example 10

Reaction of [Me$_2$NN]Cu(ethylene) and N$_3$Ar$^F$ Determination of X-Ray Structure for Deactivated Catalyst A solution of N$_3$Ar$^F$ (0.063 g, 0.25 mmol) in 2 mL of toluene was added dropwise to a solution of [Me$_2$NN]Cu (ethylene) (0.104 g, 0.26 mmol) in 5 mL of toluene. The solution color changed from yellow to yellow-green during the addition. After stirring for 30 min., the volatiles were removed in vacuo and the residue was extracted with ether (10 mL). The mixture was filtered through Celite, and the filtrate was concentrated and cooled to −35° C. to afford a few pale yellow crystals suitable for X-ray diffraction.

Example 11

[Me$_2$NN$_B$]Cu(3,3-dimethylbutene)

Powdered [Cu(CH$_3$CN)$_4$]$^+$BF$_4^-$ (0.534 g, 1.433 mmol) was added to a solution of 3,3-dimethylbutene (0.241 g, 2.866 mmol) in 10 mL ether at −40° C. Li[Me$_3$NN] (0.860 g, 1.433 mmol) was dissolved in 10 mL ether at −40° C. and added to the former suspension for 15 minutes. After stirring for 1 hour at room temperature, the volatiles were removed in vacuo and the residue was extracted with pentane (25 mL) and filtered through Celite. The filtrate was concentrated and cooled to ±40° C. to afford 0.799 g (75%) of bright yellow crystals. $^1$H NMR (C$_6$D$_6$): δ 5.382 (s, 1, backbone-CH). Signals are present for [Me$_3$NN]Cu(benzene) as well as free 3,3-dimethylbutene indicating dissociation of the olefin from the [Me$_3$NN]Cu fragment.

Example 12

Computational Experiments

The preliminary DFT calculations employed the Becke-Perdew exchange correlation functional using the Amsterdam Density Functional suite of programs (ADF 2002.03). See (a) Becke, A. *Phys. Rev. A* 1988, 38, 3098; (b) Perdew, J. P. *Phys. Rev. B* 1986, 34, 7406; (c) Perdew, J. P. *Phys. Rev. B* 1986, 33, 8822; (d) te Velde, G.; Bickelhaupt, F. M.; Baerends, E. J.; Fonseca Guerra, C.; Van Gisbergen, S. J. A.; Snijders, J. G.; Ziegler, T. *J. Comput. Chem.* 2001, 22, 931 and references therein; (e) Fonseca Guerra, C.; Snijders, J. G.; te Velde, G.; Baerends, E. J.; Acc., T. C. *Theor. Chem. Acc.* 1998, 99, 391; and (f) ADF2002.03, SCM, Theoretical Chemistry, Vrije Universieit, Amsterdam, The Netherlands, http://www.scm.com. Slater-type orbital (STO) basis sets employed for H, C, and N atoms were of triple-ζ quality augmented with two polarization functions (TZP2/ADF basis V) while an improved triple-ζ basis set with two polarization functions (TZP2+) was employed for the Co atom. The 1 s electrons of C and N as well as the 1s-2p electrons of Co were treated as frozen core. The VWN (Vosko, Wilk, and Nusair) functional was used for LDA (local density approximation). See Vosko, S. H.; Wilk, L.; Nusair, M. *Can. J. Phys.* 1980, 58, 1200.

Figure 9:
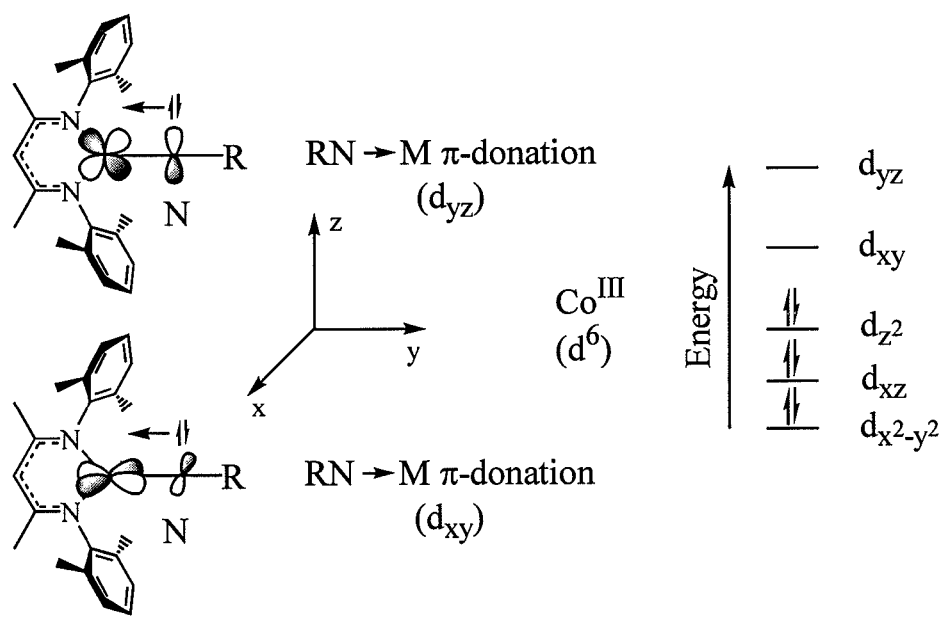
FIG. 9 depicts a schematic representation of metal-imide multiple bonding for linear imides $[Me_2NN]Co{=}NR$ based on DFT calculations (same coordinate system as in calculations).
Figure 11:
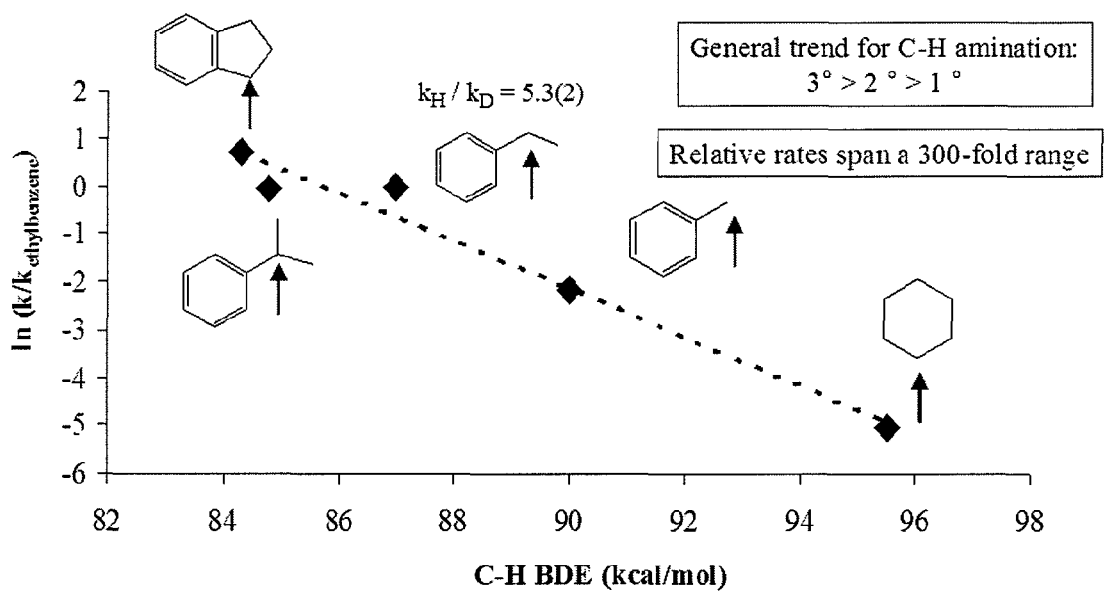
FIG. 11 depicts the rates of C—H insertion for a number of different C—H containing substrates (all relative to the rate for ethylbenzene) as a function of the bond dissociation energy (BDE) of the particular C—H bond.
Figure 13:
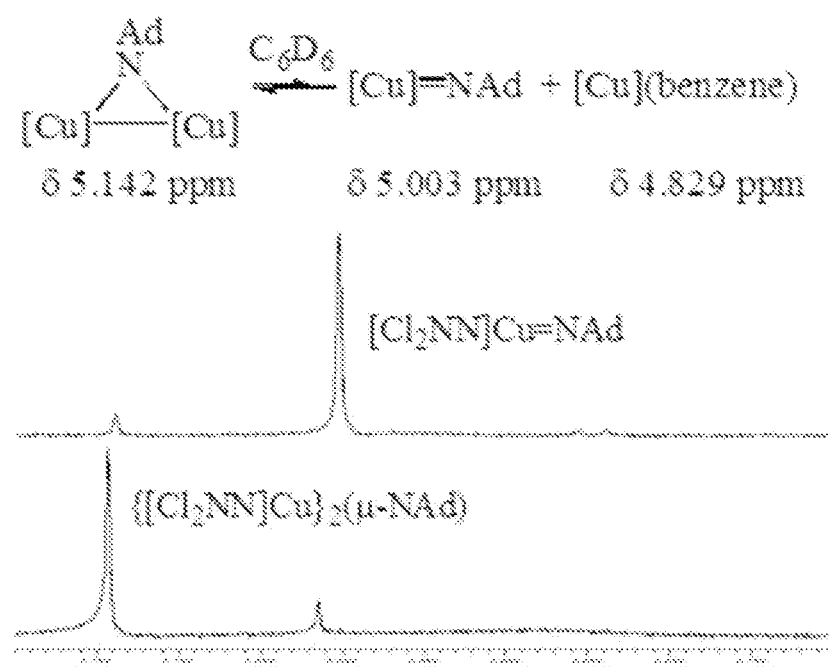
FIG. 13 depicts an equilibrium between $\{[Cl_2NN]Cu\}_2(\mu\text{-NAd})$ and $[Cl_2NN]Cu{=}NAd$ in $C_6D_6$, and $^1H$ NMR data for the two copper-nitrene complexes.

Employing typical bond distances and angles for the β-diketiminate ligand and the imido t-butyl substituent as well as Co—N and N—Co—N angles similar to those determined in the X-ray structure of [Me$_2$NN]Co≡NAd (13), coordinates for a model of [Me$_2$NN]Co≡NBu$^t$ possessing C$_s$ symmetry (z->-z) were developed in the coordinate system shown in FIG. 9. These coordinates were optimized and converged to give a structure whose Co—N distances and N—Co—N angles are in excellent agreement with the experimentally determined structure of [Me$_2$NN]Co≡NAd (Table 3). In this preliminary calculation to identify the electronic structure of a C$_{2v}$-like [Me$_2$NN]Co≡NR species possessing a linear Co≡N—R linkage (consistent with the observed solution structure of 4 at −80° C.), bending of the imido substituent as well as the slight displacement of the Co atom from the N$_3$-plane observed in the X-ray structure of 4 were not considered.

TABLE 3

Selected calculated vs. experimentally determined distances (Å) and angles (°).

| Parameter | Calculated | Experiment |
|---|---|---|
| Co1-N3 | 1.622 | 1.624(4) |
| Co1-N1 | 1.856 | 1.854(4) |
| Co1-N2 | 1.856 | 1.855(4) |
| N1-Co1-N2 | 92.5 | 92.76(17) |
| N1-Co-N3 | 133.7 | 131.9(2) |
| N2-Co-N3 | 133.7 | 132.3(2) |

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:
1. A compound represented by Formula IV:

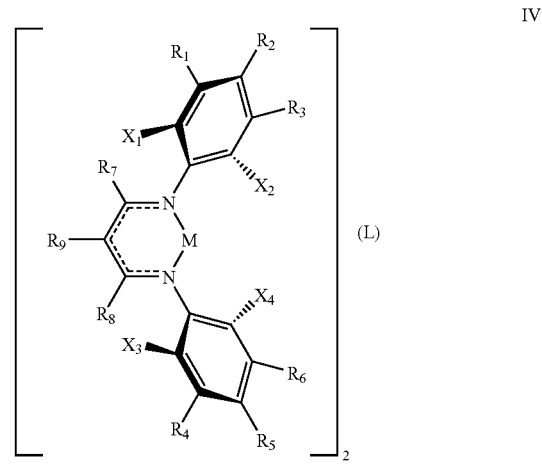

wherein,
R$_1$-R$_6$ and R$_9$ represents independently for each occurrence H, alkyl, aryl, aralkyl, halogen, CN, or CF$_3$;
R$_7$ and R$_8$ represent independently for each occurrence H, alkyl, aryl, aralkyl, or halogen;
X$_1$-X$_4$ represents independently for each occurrence hydrogen, halogen or perhaloalkyl;
L is a Lewis base selected from the group consisting of an aromatic compound, a μ-nitrene, and two μ-oxygen atoms; and
M is Cu or Co.

2. The compound of claim 1, wherein M is Cu.
3. The compound of claim 1, wherein M is Co.
4. The compound of claim 1, wherein R$_7$-R$_9$ represents independently for each occurrence H, Me, Ph, or t-Bu.
5. The compound of claim 1, wherein R$_7$ and R$_8$ represent t-Bu.
6. The compound of claim 1, wherein X$_1$-X$_4$ are independently for each occurrence halogen or perfluoroalkyl.

7. The compound of claim 1, wherein $X_1$-$X_4$ are independently for each occurrence Cl, I, Br, or $CF_3$.

8. The compound of claim 1, wherein $X_1$-$X_4$ are independently for each occurrence Cl.

9. The compound of claim 1, wherein $X_1$-$X_4$ are independently for each occurrence $CF_3$.

10. The compound of claim 1, wherein M is Cu, and $X_1$-$X_4$ are independently for each occurrence Cl.

11. The compound of claim 1, wherein M is Cu, and $X_1$-$X_4$ are independently for each occurrence $CF_3$.

12. The compound of claim 1, wherein L is an aromatic compound.

13. The compound of claim 1, wherein L is toluene.

14. The compound of claim 1, wherein L is two μ-oxygen atoms.

15. The compound of claim 1, wherein M is Cu, $X_1$-$X_4$ are independently for each occurrence Cl, and L is toluene.

16. The compound of claim 1, wherein M is Cu, $X_1$-$X_4$ are independently for each occurrence $CF_3$, and L is toluene.

17. A method of C—H bond amination depicted in Scheme A:

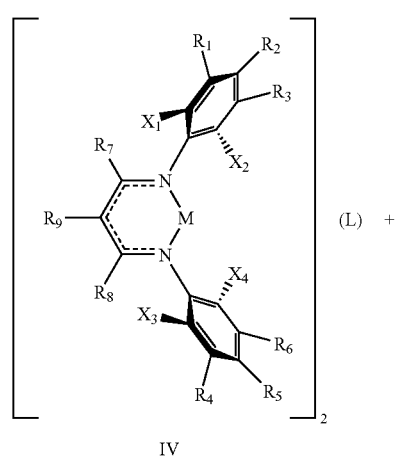

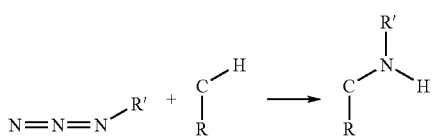

wherein,

R represents alkyl, alkenyl, alkynyl, aralkyl, aryl or heteroaryl;

R' represents alkyl, alkenyl, alkynyl, aralkyl, aryl or heteroaryl;

$R_1$-$R_9$ represents independently for each occurrence H, alkyl, aryl, aralkyl, halogen, CN, or $CF_3$;

$X_1$-$X_4$ represents independently for each occurrence hydrogen, halogen or perhaloalkyl;

L is a Lewis base selected from the group consisting of an aromatic compound, a μ-nitrene, and two μ-oxygen atoms; and M is Cu or Co.

18. A method of C—H bond amidation depicted in Scheme B:

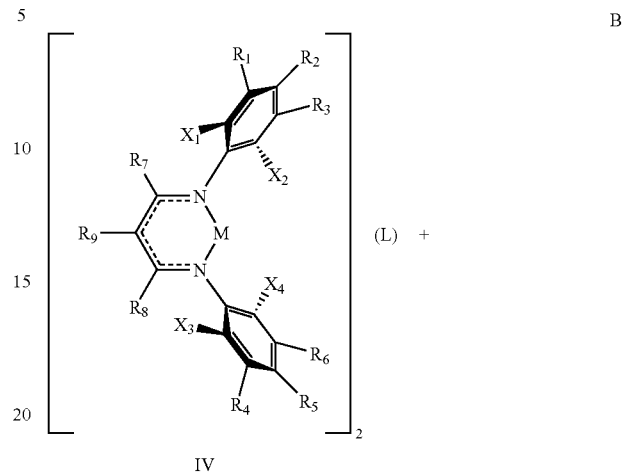

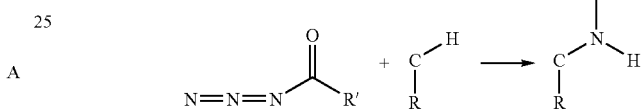

wherein,

R represents alkyl, alkenyl, alkynyl, aralkyl, aryl or heteroaryl;

R' represents alkyl, alkenyl, alkynyl, aralkyl, aryl or heteroaryl;

$R_1$-$R_9$ represents independently for each occurrence H, alkyl, aryl, aralkyl, halogen, CN, or $CF_3$;

$X_1$-$X_4$ represents independently for each occurrence hydrogen, halogen or perhaloalkyl;

L is a Lewis base selected from the group consisting of an aromatic compound, a μ-nitrene, and two μ-oxygen atoms; and M is Cu or Co.

19. A method of olefin aziridination depicted in Scheme C:

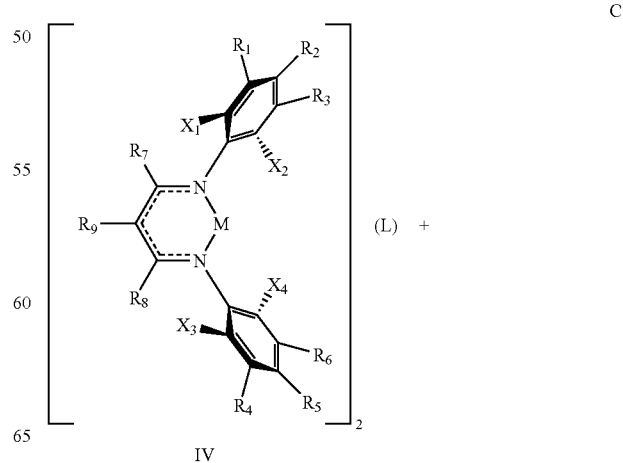

-continued

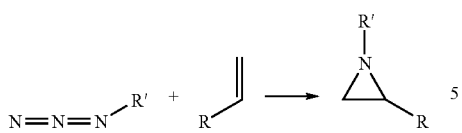

wherein,

R represents alkyl, alkenyl, alkynyl, aralkyl, aryl or heteroaryl;

R' represents alkyl, alkenyl, alkynyl, aralkyl, aryl or heteroaryl;

$R_1$-$R_9$ represents independently for each occurrence H, alkyl, aryl, aralkyl, halogen, CN, or $CF_3$;

$X_1$-$X_4$ represents independently for each occurrence hydrogen, halogen or perhaloalkyl;

L is a Lewis base selected from the group consisting of an aromatic compound, a μ-nitrene, and two μ-oxygen atoms; and M is Cu or Co.

20. A method of C—H bond amidation depicted in Scheme D:

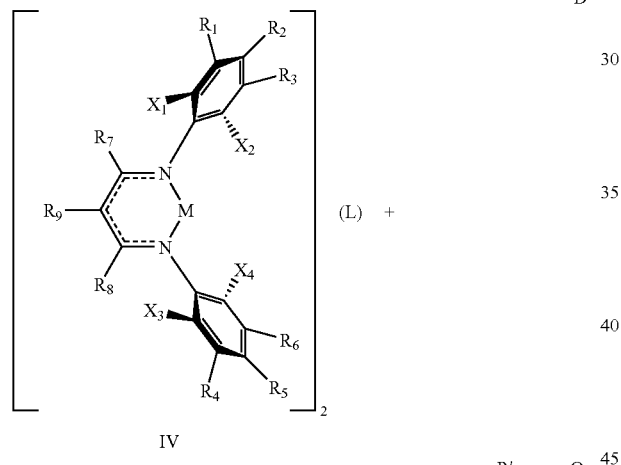

IV

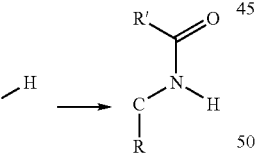

wherein,

R represents alkyl, alkenyl, alkynyl, aralkyl, aryl or heteroaryl;

R' represents alkyl, alkenyl, alkynyl, aralkyl, aryl or heteroaryl;

$R_1$-$R_9$ represents independently for each occurrence H, alkyl, aryl, aralkyl, halogen, CN, or $CF_3$;

$X_1$-$X_4$ represents independently for each occurrence hydrogen, halogen or perhaloalkyl;

L is a Lewis base selected from the group consisting of an aromatic compound, a μ-nitrene, of and two μ-oxygen atoms; and M is Cu or Co.

21. The compound of claim 1, wherein the compound is selected from the group consisting of

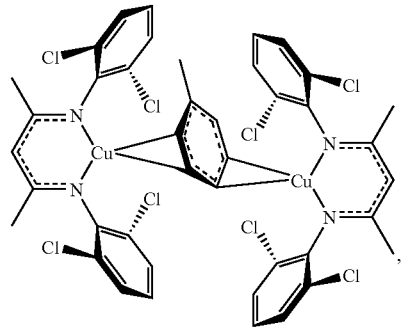

,

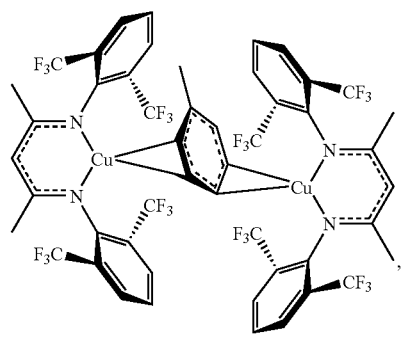

,

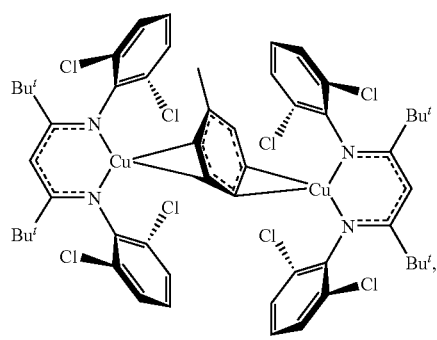

,

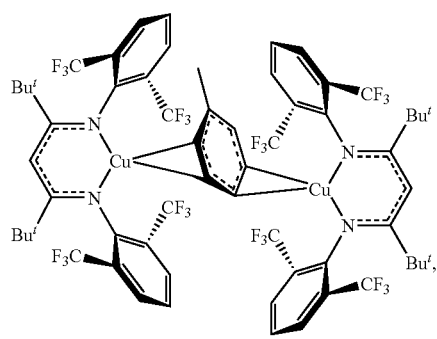

,

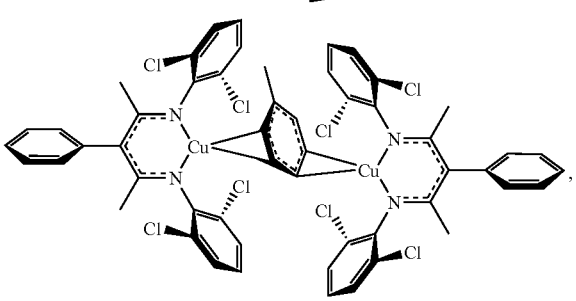

,

53
-continued
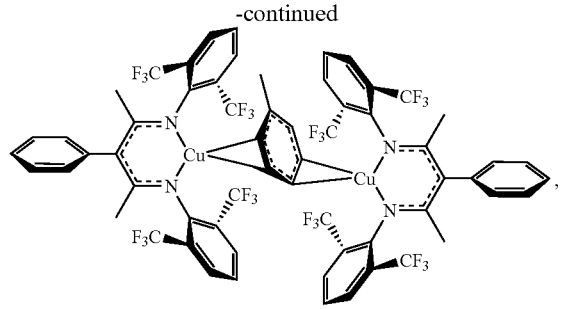
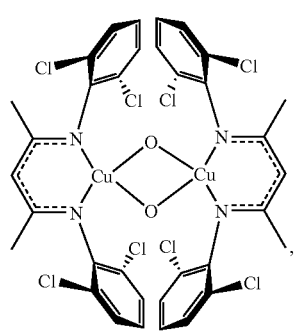
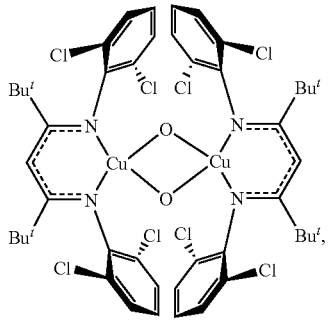
54
-continued
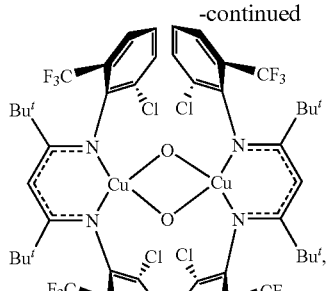
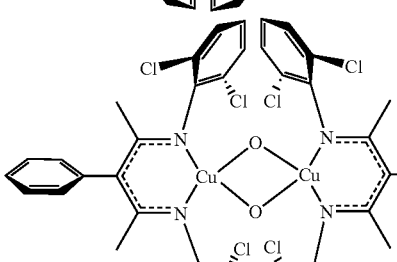, and
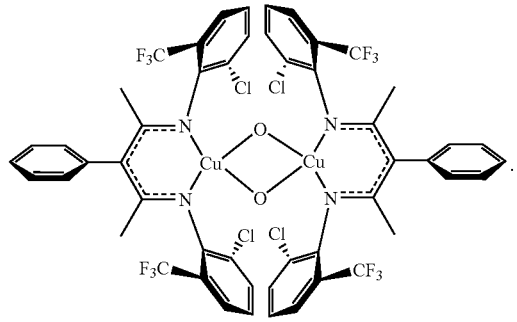.
22. The compound of claim 1, wherein L is a μ-nitrene.
23. The compound of claim 22, wherein M is Cu.
24. The compound of claim 12, wherein M is Cu.
25. The compound of claim 13, wherein M is Cu.
26. The compound of claim 14, wherein M is Cu.
* * * * *